(12) United States Patent
Oliver et al.

(10) Patent No.: US 9,022,967 B2
(45) Date of Patent: May 5, 2015

(54) IMPLANT DEVICE, TOOL, AND METHODS RELATING TO TREATMENT OF PARANASAL SINUSES

(75) Inventors: Christopher Lee Oliver, Lakewood, CO (US); Donald F. Schomer, Englewood, CO (US); Harry Ross, Boulder, CO (US); William W. Cimino, Louisville, CO (US); Brian James Willoughby, Denver, CO (US)

(73) Assignee: Sinopsys Surgical, Inc., Boulder, CO (US)

( * ) Notice: Subject to any disclaimer, the term of this patent is extended or adjusted under 35 U.S.C. 154(b) by 638 days.

(21) Appl. No.: 13/225,213

(22) Filed: Sep. 2, 2011

(65) Prior Publication Data

US 2012/0089071 A1    Apr. 12, 2012

Related U.S. Application Data

(60) Provisional application No. 61/404,716, filed on Oct. 8, 2010, provisional application No. 61/528,058, filed on Aug. 26, 2011.

(51) Int. Cl.
| | |
|---|---|
| *A61M 5/00* | (2006.01) |
| *A61M 31/00* | (2006.01) |
| *A61F 9/007* | (2006.01) |
| *A61M 27/00* | (2006.01) |

(52) U.S. Cl.
CPC ............ *A61M 31/00* (2013.01); *A61F 9/00772* (2013.01); *A61M 27/002* (2013.01)

(58) Field of Classification Search
USPC ................................ 604/8–10, 294; 606/4–6
See application file for complete search history.

(56) References Cited

U.S. PATENT DOCUMENTS

| | | | |
|---|---|---|---|
| 3,726,284 | A | 4/1973 | Parker |
| 3,948,272 | A | 4/1976 | Guibor |
| 4,921,485 | A | 5/1990 | Griffiths |
| 5,169,386 | A | 12/1992 | Becker et al. |
| 5,345,948 | A | 9/1994 | O'Donnell, Jr. |
| 6,041,785 | A | 3/2000 | Webb |
| 6,083,188 | A | 7/2000 | Becker |
| 6,878,165 | B2 | 4/2005 | Makino |
| 6,966,888 | B2 | 11/2005 | Cullen et al. |

(Continued)

FOREIGN PATENT DOCUMENTS

| | | |
|---|---|---|
| EP | 0631793 A1 | 1/1995 |
| WO | 2010096822 A2 | 8/2010 |
| WO | 2012048278 A2 | 4/2012 |

OTHER PUBLICATIONS

Sadeghi, Nader, M.D. et al. Transnasal Endoscopic Medial Maxillectomy for Inverting Papilloma. Laryngoscope (2003) 113:749-753.*

(Continued)

*Primary Examiner* — Melanie Hand
(74) *Attorney, Agent, or Firm* — Marsh Fischmann & Breyfogle LLP

(57) ABSTRACT

An implant device is configured to be implanted in a fistula to fluidly connect the lacrimal apparatus and a paranasal sinus. A surgical tool has an implant the implant device mounted on a carrier. Various methods involve a fistula between the lacrimal apparatus and a paranasal sinus. A kit includes an entry device for use to form a fistula and an implant tool for use to implant an implant device following formation of a fistula.

74 Claims, 24 Drawing Sheets

(56) References Cited

U.S. PATENT DOCUMENTS

| | | | |
|---|---|---|---|
| 7,156,821 B2 | 1/2007 | Dohlman | |
| 7,169,163 B2 | 1/2007 | Becker | |
| 7,361,168 B2 | 4/2008 | Makower et al. | |
| 7,410,480 B2 | 8/2008 | Muni et al. | |
| 7,419,497 B2 | 9/2008 | Muni et al. | |
| 7,462,175 B2 | 12/2008 | Chang et al. | |
| 7,500,971 B2 | 3/2009 | Chang et al. | |
| D590,935 S | 4/2009 | Becker | |
| 7,547,323 B2 | 6/2009 | Lavigne | |
| 7,559,925 B2 | 7/2009 | Goldfarb et al. | |
| 7,641,644 B2 | 1/2010 | Chang et al. | |
| 7,645,272 B2 | 1/2010 | Chang et al. | |
| 7,654,997 B2 | 2/2010 | Makower et al. | |
| 7,713,255 B2 | 5/2010 | Eaton et al. | |
| 7,720,521 B2 | 5/2010 | Chang et al. | |
| 7,727,186 B2 | 6/2010 | Makower et al. | |
| 7,727,226 B2 | 6/2010 | Chang et al. | |
| 7,758,534 B2 | 7/2010 | Pearson | |
| 7,771,409 B2 | 8/2010 | Chang et al. | |
| 7,785,315 B1 | 8/2010 | Muni et al. | |
| 7,803,150 B2 | 9/2010 | Chang et al. | |
| 7,846,124 B2 | 12/2010 | Becker | |
| 2002/0032444 A1 | 3/2002 | Mische | |
| 2002/0107579 A1 | 8/2002 | Makino | |
| 2004/0116958 A1* | 6/2004 | Gopferich et al. | 606/199 |
| 2004/0204704 A1 | 10/2004 | Tamplenizza et al. | |
| 2004/0254516 A1 | 12/2004 | Murray et al. | |
| 2005/0197614 A1 | 9/2005 | Pritchard et al. | |
| 2005/0240143 A1 | 10/2005 | Dohlman | |
| 2005/0245906 A1 | 11/2005 | Makower et al. | |
| 2006/0063973 A1 | 3/2006 | Makower et al. | |
| 2006/0251575 A1 | 11/2006 | Morgenstern | |
| 2006/0276738 A1 | 12/2006 | Becker | |
| 2007/0005120 A1 | 1/2007 | Villacampa et al. | |
| 2007/0112291 A1 | 5/2007 | Borgesen | |
| 2007/0129751 A1 | 6/2007 | Muni et al. | |
| 2007/0135789 A1 | 6/2007 | Chang et al. | |
| 2007/0167682 A1 | 7/2007 | Goldfarb et al. | |
| 2007/0208252 A1 | 9/2007 | Makower | |
| 2007/0208301 A1 | 9/2007 | Evard et al. | |
| 2007/0249896 A1 | 10/2007 | Goldfarb et al. | |
| 2007/0255263 A1 | 11/2007 | Sugimoto | |
| 2007/0276314 A1 | 11/2007 | Becker | |
| 2007/0282305 A1 | 12/2007 | Goldfarb et al. | |
| 2007/0293726 A1 | 12/2007 | Goldfarb et al. | |
| 2007/0293727 A1 | 12/2007 | Goldfarb et al. | |
| 2008/0082037 A1 | 4/2008 | Pearson | |
| 2008/0097154 A1 | 4/2008 | Makower et al. | |
| 2008/0097354 A1 | 4/2008 | Lavigne | |
| 2008/0097514 A1 | 4/2008 | Chang et al. | |
| 2008/0103361 A1 | 5/2008 | Makower et al. | |
| 2008/0103521 A1 | 5/2008 | Makower et al. | |
| 2008/0119693 A1 | 5/2008 | Makower et al. | |
| 2008/0125626 A1 | 5/2008 | Chang et al. | |
| 2008/0125805 A1 | 5/2008 | Mische | |
| 2008/0132938 A1 | 6/2008 | Chang et al. | |
| 2008/0154237 A1 | 6/2008 | Chang et al. | |
| 2008/0154250 A1 | 6/2008 | Makower et al. | |
| 2008/0195041 A1 | 8/2008 | Goldfarb et al. | |
| 2008/0228085 A1 | 9/2008 | Jenkins et al. | |
| 2008/0234720 A1 | 9/2008 | Chang et al. | |
| 2008/0275483 A1 | 11/2008 | Makower et al. | |
| 2008/0281156 A1 | 11/2008 | Makower et al. | |
| 2008/0287908 A1 | 11/2008 | Muni et al. | |
| 2008/0306428 A1 | 12/2008 | Becker | |
| 2008/0319424 A1 | 12/2008 | Muni et al. | |
| 2009/0005763 A1 | 1/2009 | Makower et al. | |
| 2009/0028923 A1 | 1/2009 | Muni et al. | |
| 2009/0030274 A1 | 1/2009 | Goldfarb et al. | |
| 2009/0099626 A1 | 4/2009 | de Juan, Jr. et al. | |
| 2009/0104248 A1 | 4/2009 | Rapacki et al. | |
| 2009/0105749 A1 | 4/2009 | de Juan, Jr. et al. | |
| 2009/0187098 A1 | 7/2009 | Makower et al. | |
| 2009/0198216 A1 | 8/2009 | Muni et al. | |
| 2009/0204142 A1 | 8/2009 | Becker | |
| 2009/0221988 A1* | 9/2009 | Ressemann et al. | 604/514 |
| 2009/0240112 A1 | 9/2009 | Goldfarb et al. | |
| 2009/0240237 A1 | 9/2009 | Goldfarb et al. | |
| 2009/0275882 A1 | 11/2009 | Lavigne | |
| 2009/0275903 A1 | 11/2009 | Lavigne | |
| 2009/0281621 A1 | 11/2009 | Becker | |
| 2009/0312745 A1 | 12/2009 | Goldfarb et al. | |
| 2010/0034870 A1 | 2/2010 | Sim et al. | |
| 2010/0042046 A1 | 2/2010 | Chang et al. | |
| 2010/0076269 A1 | 3/2010 | Makower et al. | |
| 2010/0099946 A1 | 4/2010 | Jenkins et al. | |
| 2010/0100181 A1 | 4/2010 | Makower et al. | |
| 2010/0106255 A1 | 4/2010 | Dubin | |
| 2010/0114066 A1 | 5/2010 | Makower et al. | |
| 2010/0121308 A1 | 5/2010 | Muni et al. | |
| 2010/0174138 A1 | 7/2010 | Chang et al. | |
| 2010/0174308 A1 | 7/2010 | Chang et al. | |
| 2010/0198247 A1 | 8/2010 | Chang et al. | |
| 2010/0210901 A1 | 8/2010 | Makower et al. | |
| 2010/0268245 A1 | 10/2010 | Chang et al. | |
| 2010/0274204 A1 | 10/2010 | Rapacki et al. | |
| 2010/0298862 A1 | 11/2010 | Chang et al. | |
| 2010/0317969 A1 | 12/2010 | Becker | |
| 2011/0004057 A1 | 1/2011 | Goldfarb et al. | |
| 2011/0060214 A1 | 3/2011 | Makower | |
| 2011/0105989 A1 | 5/2011 | Becker | |
| 2011/0112512 A1 | 5/2011 | Muni et al. | |
| 2011/0224680 A1 | 9/2011 | Barker | |
| 2011/0276131 A1 | 11/2011 | De Juan, Jr. et al. | |
| 2012/0245539 A1 | 9/2012 | Zarins et al. | |
| 2013/0274647 A1 | 10/2013 | Oliver et al. | |
| 2014/0012309 A1 | 1/2014 | Keith et al. | |

OTHER PUBLICATIONS

Dictionary Definition for 'inject'. https://www.google.com/search?q=inject&sourceid=ie7&rls=com.microsof:en-us:IE-Address&ie=&oe=&gws_rd=ssl.*

Mangan, BG et al. Bilateral Nasolacrimal Duct Atresia in a Cria. Veterinary Opthalmology (2008) 11, 1, 49-54.

Giuliano, EA et al. Dacryocystomaxillorhinostomy for Chronic Dacryocystitis in a Dog. Veterinary Opthalmology (2006) 9, 2, 89-94.

Wilson, DG et al. Surgical Reconstruction of the Nasolacrimal System in the Horse. Equine Veterinary Science (1991) vol. II, No. 4, pp. 232-234.

Steinmetz, A et al. Surgical Removal of a Dermoid Cyst From the Bony Part of the Nasolacrimal Duct in a Scottish Highland Cattle Heifer. Veterinary Opthalmology (2009) 12, 4, 259-262.

McIlnay, TR et al. Use of Canaliculorhinostomy for Repair of Nasolacrimal Duct Obstruction in a Horse. JAVMA (2001) vol. 218, No. 8. Scientific Reports: Clinical Report. 1323-1324.

Gionfriddo JR. The nasolacrimal system. In: Textbook of Small Animal Surgery 3rd edition. 2003, Slatter DM ed. Saunders, Philadelphia PA, pp. 1356-1358.

* cited by examiner

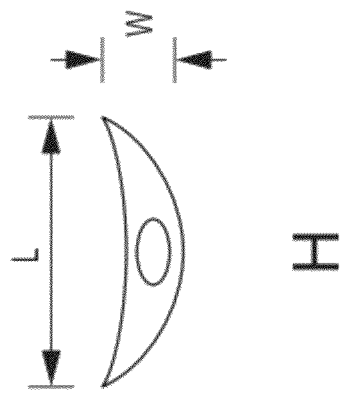
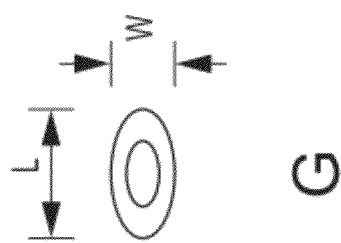
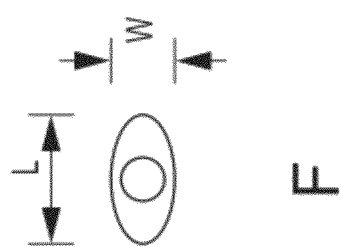
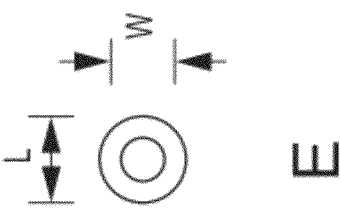
FIG. 11

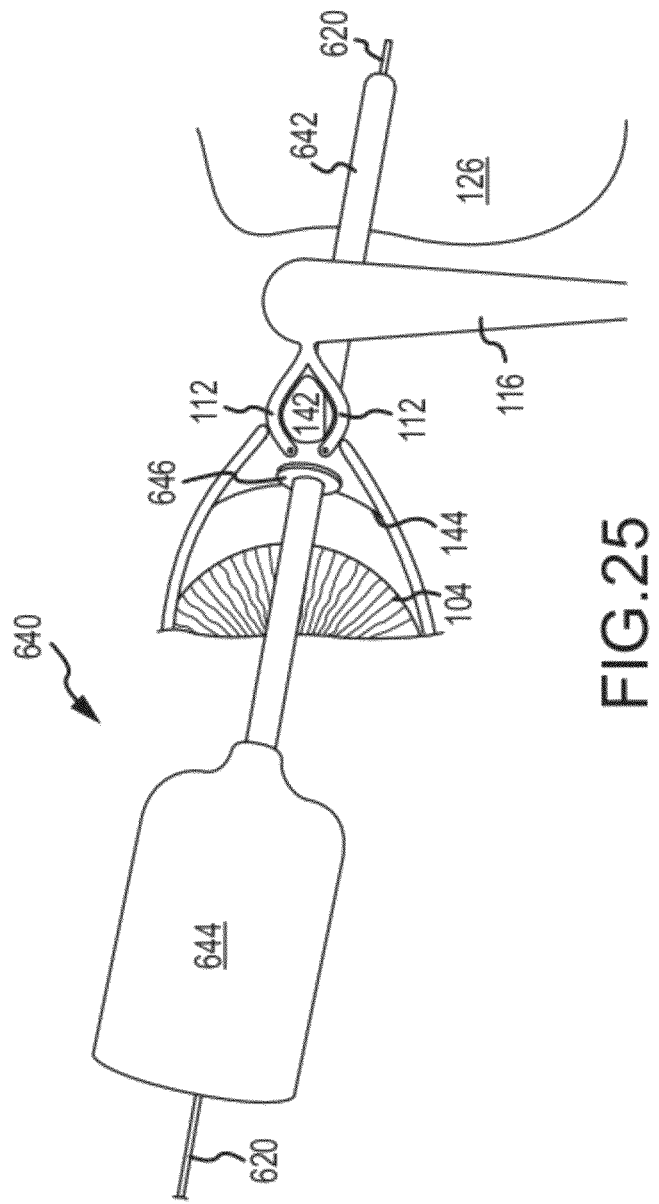

IMPLANT DEVICE, TOOL, AND METHODS RELATING TO TREATMENT OF PARANASAL SINUSES

CROSS-REFERENCE TO RELATED APPLICATIONS

This application claims the benefit of U.S. provisional patent application No. 61/404,716 filed Oct. 8, 2010 and U.S. provisional patent application No. 61/528,058 filed Aug. 26, 2011, the contents of each of which is incorporated herein by reference as if each and every portion thereof were set forth herein.

FIELD OF THE INVENTION

The invention relates to treatment of conditions of the paranasal sinuses, including with respect to implant devices, surgical tools and methods.

BACKGROUND OF THE INVENTION

In the United States alone, 35 million people a year are treated for sinus infections, or sinusitis, and 7 million of those will suffer from chronic sinusitis and will have minimal response to prescription drug therapies. Current surgical interventions may be expected to, at best, offer only moderate symptomatic improvement but no cure.

Current drug therapies include oral administration as pills and nasal topical administration, neither of which is conducive to delivering adequate concentration of medication to the involved paranasal sinus. In addition to medication, frequent sinus irrigation can be helpful in flushing out debris, irritants and obstructing viscous fluids, but patients are generally not able to adequately perform this procedure at home.

For patients with particularly severe symptoms, surgical drainage may be the only additional option. An early surgical procedure was the Caldwell-Luc procedure, which involves creating a permanent fistula from the base of the paranasal sinus into the oral cavity above the front upper incisors. More recently, other surgical access points to the paranasal sinuses have been attempted. A variety of endoscopic techniques have been developed that access the paranasal sinuses through the nose, including functional endoscopic sinus surgery (FESS) and balloon sinuplasty. All attempt to increase drainage, but utilize different routes or tools. None of these surgical approaches has achieved wide-spread success, and millions of chronic sinusitis patients continue to suffer long-term disability and discomfort.

SUMMARY OF INVENTION

A variety of medical treatments and medical procedures directed to the paranasal sinuses may be performed through a fistula that may be formed between the lacrimal apparatus and a paranasal sinus. Such a fistula provides direct access from the lacrimal apparatus to the paranasal sinus in a minimally invasive manner. Such direct access permits drugs to be conveniently administered for local treatment in the paranasal sinus, rather than having to rely on systemic drug treatments. Such direct access permits irrigation fluids to be conveniently introduced into the paranasal sinus. Such access permits fluids to be conveniently removed from the paranasal sinus. Such access permits a variety of medical procedures to be conveniently performed in the paranasal sinus.

A first aspect of the invention involves an implant device for implantation in a human to fluidly connect the lacrimal apparatus a paranasal sinus through such a fistula. The implant device has a proximal end and a distal end located at opposite longitudinal ends of the device. A conduit extends from adjacent the proximal end to adjacent the distal end. An internal passage extends between the proximal end and the distal end, and including through the conduit. The internal passage has a first end open at the proximal end of the implant device and a second end open at the distal end of the implant device. The implant device includes a length longitudinally along the device between the proximal end and the distal end that is in a range of from 2 millimeters to 50 millimeters. A width of the internal passage transverse to the length is in a range of from 0.25 millimeter to 5 millimeters. The implant device is configured to be implanted to fluidly connect the lacrimal apparatus to the paranasal sinus through the fistula so that when the implant device is implanted: the proximal end is disposed with the first end of the internal passage opening in the lacrimal apparatus; the distal end is disposed in the paranasal sinus with the second end of the internal passage opening in the paranasal sinus; and the conduit is disposed through the fistula.

A number of feature refinements and additional features are applicable to the first aspect of the invention. These feature refinements and additional features may be used individually or in any combination. As such, each of the following features may be, but are not required to be, used within any other feature or combination of features of the first aspect or any other aspects of the invention.

The conduit may be configured so that an exterior of the conduit comprises an anchoring surface feature which assists to anchor the implant device when the device is implanted. The anchoring surface feature includes protrusion areas and recess areas. The implant device may be configured so that when implanted the conduit is disposed through the fistula with at least a portion of the recess areas disposed within the fistula and with at least a portion of the protrusion areas disposed in the fistula and engaging tissue exposed within the fistula to anchor the implant device. The structural and mechanical characteristics of protrusion occurrences in the protrusion areas may affect anchoring performance of the protrusion areas. The height of the protrusion areas relative to the recess areas may affect anchoring effectiveness when the implant device is implanted. A larger height may provide greater anchor effectiveness, but also may involve a larger overall width of the implant device that must be inserted into the fistula. The protrusion areas may have a height relative to the recess areas of at least 0.1 millimeter, at least 0.2 millimeter, at least 0.25 millimeter or at least 0.3 millimeter. The protrusions areas may have a height relative to the recess areas of no greater than 2 millimeters, no greater than 1.5 millimeter, no greater than 1 millimeter, no greater than 0.75 millimeter, no greater than 0.5 millimeter or no greater than 0.4 millimeter. The height may be of particular protrusion occurrences relative to adjacent areas of recesses. Protrusion occurrences are also referred to herein as anchor protrusions. Such anchor protrusions may be configured to flexibly deform when the conduit is inserted through the fistula for implantation, for example to flexibly deform in a direction opposite the direction of insertion when the anchor protrusions contact tissue disposed in the fistula during insertion. After insertion, the anchor protrusions may over time return to their original shape and extend deeper into adjacent tissue to better anchor the implant device. The mechanical properties of the anchor protrusions may be influenced by materials of construction. One preferred material of construction for the protrusion areas, and also for other portions of the implant device, is medical grade silicone, with the medical grade silicone preferably having a durometer (Shore A) in a range having a lower limit of 50 and an upper limit of 80, 70 or 60. Mechanical properties of the protrusion occurrences of the protrusion areas will also be affected by the geometry of the protrusion areas. The protrusion occurrences may have a width that tapers, or narrows, in a direction from a base toward a top of the protrusion occurrences, with the base being a portion of a protrusion occurrence disposed toward the internal passage of the conduit and a top of the protrusion occurrence being the extremity of the protrusion occurrence away from the internal passage of the conduit. The width may be transverse to the length of the conduit. The protrusion occurrences may have a width at the base that is no larger than 2 millimeters, no larger than 1.5 millimeters, no larger than 1.25 millimeters or no larger than 1 millimeter. One or more of the protrusion occurrences may have a width at the base that is at least 0.2 millimeter, at least 0.3 millimeter, at least 0.5 millimeter, at least 0.75 millimeter or at least 1 millimeter. The protrusion occurrences may have a width adjacent the top that is no larger than 0.75 times width at the base, no larger than 0.5 times the width at the base, or no larger than 0.25 times the width at the base. The protrusion occurrences may have a width midway between the base and the top that is no larger than 0.8 times the width of the base, no larger than 0.7 times the width of the base, no larger than 0.6 times the width of the base or no larger than 0.5 times the width at the base.

The protrusion areas may be provided by a single protrusion occurrence feature located to correspond with the interior of the fistula when the implant device is implanted. In more preferred implementations, the protrusion areas include multiple protrusion occurrences spaced on the exterior of the conduit. The protrusion occurrences may have s a center-to-center spacing, in one or more directions, of at least 0.5 millimeter, at least 0.75 millimeter, at least 1 millimeter or at least 1.75 millimeters. The protrusion occurrences may have a center-to-center spacing of no greater than 2.5 millimeters, no greater than 2 millimeters or no greater than 1.75 millimeters. The protrusion occurrences may have a center-to-center spacing longitudinally along the conduit. The protrusion occurrences may have a center-to-center spacing that is at least 0.5 times the base width of the protrusion occurrences, or at least 1 times the base width of the protrusion occurrences or at least 2 times the base width of the protrusion occurrences. The protrusion occurrences may have a center-to-center spacing that is no more than 5 times a base width of the protrusion occurrences, no more than 3 times a base width of the protrusion occurrences or no more than 2 times a base width of the protrusion occurrences.

The protrusion areas may be located on a longitudinal portion of the conduit that includes at least a portion of the conduit that will be disposed within a fistula when the implant device is implanted. The protrusion areas may be on a longitudinal portion of the conduit that extends for at least 2 millimeters along the length of the implant device, that extends for at least 3 millimeters along the length of the implant device, that extends for at least 4 millimeters along the length of the implant device, that extends for at least 5 millimeters along the length of the implant device or that extends for at least 8 millimeters along the length of the implant device. A longitudinal portion of the conduit including the protrusion areas may be no longer than 20 millimeters, no longer than 15 millimeters or no longer than 10 millimeters. A longitudinal portion of the conduit including the protrusion areas may be disposed at least 2 millimeters from the proximal end of the device, at least 3 millimeters from the proximal end of the device, or at least 4 millimeters from the proximal end of the device. When the implant device has a head, a longitudinal portion of the conduit including the protrusions may be disposed at least 1 millimeter, at least 2 millimeters or at least 3 millimeters from the head. Providing significant distance between the head and commencement of the protrusion areas permits the head to better "float" on the surface of tissue, which may enhance patient comfort and device performance. The protrusion areas may be disposed along a longitudinal portion of the conduit with the protrusion areas covering no more than 35% of the area along that longitudinal portion of the conduit, no more than 25% of the area along that longitudinal portion of the conduit or not more than 20% of the area along that longitudinal portion of the conduit. Providing significant spacing between protrusion occurrences may permit better engagement of tissue by the anchoring surface feature.

The protrusion areas may comprise at least one circumferential ridge. By circumferential ridge is meant a ridge that extends around an entire circumference of the conduit. The protrusion area may comprise at least two, at least three or at least five circumferential ridges. The protrusion areas may comprise a spiral ridge. Such a spiral ridge may extend along a longitudinal portion of the conduit. The protrusion areas may comprise a knob or may comprise multiple knobs. The anchoring surface feature may comprise a textured surface, with the protrusion areas comprising protruding portions of the textured surface and the recess areas comprising recess portions of the textured surface.

The length of the implant device may be selected within the general range stated above to provide sufficient conduit length for extending through the entire length of the fistula plus any extension distance desired in the lacrimal apparatus proximal to the fistula and in the paranasal sinus distal to the fistula. The length of the conduit may be in a range having a lower limit of 2 millimeters, 3 millimeters, 4 millimeters, 5 millimeters or 8 millimeters and an upper limit of 50 millimeters, 40 millimeters, 30 millimeters, 20 millimeters, 15 millimeters or 10 millimeters. One preferred range for some implementations when the fistula is between the orbit and the ethmoid sinus or the maxillary sinus is for the length of the implant device to be in a range of from 5 millimeters to 20 millimeters, with a range of from 8 millimeters to 15 millimeters being more preferred. By length of the implant device it is meant the dimension longitudinally along the device from the proximal end to the distal end, and may be along a longitudinal axis through the internal passage. The length may be a straight line, for example when the internal passage is straight, or the length may be curvilinear or some other shape, for example when the internal passage is not linear. When a reference is made herein to transverse to the length, the reference is to a right angle to the longitudinal direction of the length at that point (e.g., right angle to a line of the length or to a line tangent to a curve of the length).

The implant device may advantageously be designed with a conduit of appropriate width dimensions to fit snuggly within a desired size of fistula. The implant device may have a first exterior width dimension defined by a maximum extent of the protrusion areas transverse to the length of the device, with the exterior width being within a range having a lower limit of 0.75 millimeter, 1 millimeter, 1.25 millimeters, 1.5 millimeters, 1.75 millimeters or 2 millimeters and an upper limit of 8 millimeters, 7 millimeters, 6 millimeters, 5 millimeters, 4 millimeters, 3 millimeters, 2 millimeters or 1.75 millimeters, provided of course that the upper limit must be larger than the lower limit. The conduit may have a second width dimension defined by the minimum extent of the recess areas transverse to the length of the device, and which second exterior width dimension will be smaller than the first exterior width dimension defined by the protrusion areas. The second exterior width dimension defined by the recess areas may be smaller than the exterior width dimension defined by the protrusion areas by an amount within a range having a lower limit of 0.2 millimeter, 0.25 millimeter, 0.35 millimeter or 0.5 millimeter and having an upper limit of 1.5 millimeters, 1 millimeter or 0.75 millimeter. The height of the protrusion areas may be one-half the difference between the first exterior width and the second exterior width. Either one of or each one of the first exterior width and the second exterior width may be the diameter of a circle.

The implant device may comprise a plurality of apertures through a wall of the conduit to provide fluid communication from outside of the conduit to the internal passage in the conduit. The apertures may be located on a portion of the conduit designed to be distal to the fistula and located in a paranasal sinus when the implant device is implanted. Some or all of the apertures may be located along the length of the device at least 5 millimeters from the proximal end, at least 8 millimeters end from the proximal end or at least 10 millimeters from the proximal end. The width of such an aperture may be equal to or may be smaller than a width of the portion of the internal passage into which the aperture opens.

The implant device may include a head adjacent to the conduit at the proximal end of the implant device. The implant device may be configured so that when the implant device is implanted, the head is disposed in the lacrimal apparatus, and preferably with the head located in the orbit. The head may beneficially keep the implant device from migrating through the fistula toward the paranasal sinus following implantation of the implant device. The head may comprise a flanged tissue engagement surface on a side of the head disposed toward the conduit and configured to engage tissue outside of and adjacent to the fistula when the implant device is implanted. The flanged tissue engagement surface may be a flat surface. The flanged tissue engagement surface may have non-flat surface features configured to improve seating of the surface against tissue, such as for example to inhibit rotation of the implant device within the fistula after implantation. The head may have a face surface opposite the flanged tissue engagement surface and also disposed away from the conduit and disposed away from tissue engaged by the flanged tissue engagement surface when the implant device is implanted. The face surface may be substantially flat. The face surface may be disposed at the proximal end of the implant device and the internal passage may open at the face surface. The separation distance between the face surface and the flanged tissue engagement surface may be in a range having a lower limit of 0.25 millimeter, 0.5 millimeter or 0.75 millimeter and having an upper limit of 2 millimeters, 1.5 millimeters or 1 millimeter. Such separation distance need not be constant across the flanged tissue engagement surface and face surface. A maximum separation distance between the face surface and the flanged tissue engagement surface may be referred to as the depth of the head, and such depth may be in a range described above for the separation distance between the face surface and the flanged tissue engagement surface. The flanged tissue engagement surface need not be continuous and may be divided into multiple distinct surface portions. For example, the flanged tissue engagement surface may include a first flanged portion disposed to one side of the internal passage and a second flanged surface portion disposed to a second side of the internal passage that is opposite the first side. Each of the face surface and the flanged tissue engagement surface may have a length dimension that represents a maximum separation distance between points on an outer edge of the respective surface, and may each have a width dimension that is a maximum separation distance between points on the outer edge transverse to the length dimension. The length dimensions of the face surface and the flanged tissue engagement surface may be the same or may be different. The width dimensions of the face surface and the flanged tissue engagement surface may be the same or may be different. The face surface and the flanged tissue engagement surface may have corresponding outer edges. The length dimension of any or all of the face surface, the flanged tissue engagement surface and the head may be larger than a first exterior width of the conduit defined by an extent of the protrusion areas transverse to the length of the implant device, when the implant device includes an anchoring surface feature such as summarized above. The length dimension of any or all of the face surface, the tissue engagement surface and the head may be in a range having a lower limit of 1 millimeter, 2 millimeters, 3 millimeters, 4 millimeters or 5 millimeters and an upper limit of, 10 millimeters, 8 millimeters or 7 millimeters. The width dimension of any or all of the face surface, tissue engagement surface and the head may be in a range having a lower limit of 0.5 millimeter, 1 millimeter, 1.5 millimeters or 2 millimeters and an upper limit of 5 millimeters, 4 millimeters or 3 millimeters. The length dimension of any or all of the face surface, the flanged tissue engagement surface and the head may be at least 1 millimeter, at least 2 millimeters, at least 3 millimeters or at least 4 millimeters larger than such first exterior width of the conduit defined by an extent of the protrusion areas, when the implant device includes an anchoring surface feature such as summarized above. A ratio of the length of any of or all the face surface, the flanged tissue engagement surface and the head to such a first exterior width of the conduit may be at least 2. Such a ratio may be smaller than 4. The width of any or all of the face surface, the flanged tissue engagement surface and the head may be not larger than, or may be smaller than, such a first exterior width of the conduit defined by an extent of the protrusion areas, when the implant device includes an anchoring surface feature such as summarized above. A ratio of the length dimension to the width dimension for any or all of the face surface, the flanged tissue engagement surface and the head may be in a range having a lower limit of 1, 1.5, 2 or 2.5 and an upper limit of 5, 4, 3 or 2.5, provided of course that the upper limit must be larger than the lower limit.

The internal passage may have a substantially uniform shape along the entire length of the implant device, or may have a varying shape. The internal passage may be substantially straight from the proximal end of the device to the distal end of the device. The internal passage may have a cross-section available for flow (transverse to the length of the device) that is substantially uniform from the proximal end to the distal end of the implant device. The internal passage may have a substantially circular cross-section. The internal passage may have a substantially elliptical cross-section. The width of the conduit (maximum dimension across the cross-section of the internal passage available for flow) may be in a range having a lower limit of 0.25 millimeter, 0.5 millimeter or 0.75 millimeter and 1 millimeter and an upper limit of 5 millimeters, or 4 millimeters or 3 millimeters, 2 millimeters or 1.5 millimeters.

The implant device may be configured for implantation with the conduit passing through a fistula between a location in a lacrimal apparatus within the orbit and a paranasal sinus selected from the group consisting of a frontal sinus, an ethmoid sinus, a maxillary sinus and a sphenoid sinus, with a frontal sinus, a maxillary sinus or an ethmoid sinus being preferred, with an ethmoid sinus or a maxillary sinus being more preferred, and with an ethmoid sinus being particularly preferred. The implant device may be configured for implantation with the conduit passing through a fistula between a location in the lacrimal apparatus within the nasolacrimal duct and a paranasal sinus selected from the group consisting of an ethmoid sinus and a maxillary sinus. The location within the nasolacrimal duct may be within the lacrimal sac.

The implant device may be disposed within a human body as implanted with the conduit passing through a fistula between the lacrimal apparatus and the paranasal sinus and with the proximal end located within the lacrimal apparatus and the distal end located within the paranasal sinus, with a preferred implementation including the distal end located in a paranasal sinus selected from the group consisting of an ethmoid sinus, the maxillary sinus and a frontal sinus and the proximal end located in the orbit, and more preferably with the proximal end disposed between the plica semilunaris and the lacrimal caruncle.

A second aspect of the invention is provided by a surgical tool comprising an implant device and a carrier. The carrier includes a member with a distal tip, and the member is adapted to be disposed through a fistula between the lacrimal apparatus and a paranasal cavity with the distal tip located in the paranasal cavity. The carrier also includes a hand-manipulable handle connected to the member. The implant device is mounted on the carrier between the handle and the distal tip, with the member disposed through the internal passage and with a proximal end of the implant device disposed toward the handle and a distal end of the implant device disposed toward the distal tip. The carrier is disengageable from the implant device for implant placement of the implant device disposed through the fistula.

A number of feature refinements and additional features are applicable to the second aspect of the invention. These feature refinements and additional features may be used individually or in any combination. As such, each of the following features may be, but are not required to be, used with any other feature or combination of features of the second aspect or any other aspects of the invention.

The implant device may be an implant device according to the first aspect of the invention. The implant device may be of a design other than according to the first aspect of the invention.

The distal tip of the member may be a piercing tip configured for piercing tissue to form a fistula (e.g., a sharp tip). The distal tip of the member may be a blunt tip designed to enter and advance through a fistula that has already been formed. The carrier may have an internal passage extending through the handle and the member and through which passage a guide wire may be passed to help guide the carrier to a location where an implant device is to be implanted in a fistula.

The member may be a solid member with the distal tip being a distal end of the solid member. The implant device may be mounted on the solid member with the solid member disposed through an internal passage of the implant device. The solid member may comprise a trocar or a stylet.

The member may be a hollow member. The implant device may be mounted on the hollow member with the hollow member disposed through an internal passage of the implant device. The distal tip may comprise a distal end of the hollow member. The hollow member may be a hollow needle or a cannula. The carrier may comprise a syringe hub in fluid communication with the hollow interior of the member. The syringe hub may be connected with a proximal end of the hollow member. The syringe hub may be or comprise a part of the handle. The syringe hub may be adapted for connecting with a syringe to permit performance of at least one operation selected from the group consisting of injecting fluid from the syringe through the hollow member and aspiration of fluid through the hollow member into a syringe. Such a hub may be configured to make a luer connection with a syringe. The carrier may comprise another member, which may be a solid member disposed through such a hollow member. The distal tip of the carrier may comprise a distal end of the solid member. The solid member may be slidably removable from a proximal end of the hollow member. The solid member may be disengageable from the hollow member. The solid member may be a stylet or a trocar. The solid member may have a distal end that is in the form of a blunt tip, or that together with a distal end of the hollow member may form a blunt tip.

The distal end of the member, and the distal tip, may be located at least 0.3 centimeter, at least 0.5 centimeter, at least 0.75 centimeter or at least 1 centimeter from a distal end of the implant device. The distal end of the member, and the distal tip, may be located not more than 5 centimeters, not more than 3 centimeters or not more than 2 centimeters from the distal end of the implant device. The distal end of the member, and the distal tip, may be located at least 0.75 centimeter, at least 1 centimeter or at least 2 centimeters from the proximal end of the implant device. The distal end of the member, and the distal tip, may be located not more than 7 centimeters, not more than 6 centimeters, not more than 5 centimeters, not more than 4 centimeters or not more than 3 centimeters from the proximal end of the implant device.

Other aspects of the invention are provided by various methods involving a fistula formed between the lacrimal apparatus of a human and a paranasal sinus. The fistula involved with any of these methods may be surgically formed by any appropriate technique between a location in the lacrimal apparatus of a human and a paranasal sinus. The fistula may be formed by a piercing or cutting instrument, such as for example a needle, cutting cannula, trocar or stylet. Other example techniques for forming the fistula include drills, lasers, radio frequency (RF) and ultrasound. The fistula may be formed using a surgical tool of the second aspect of the invention. The fistula may be formed by any appropriate route connecting a location in the lacrimal apparatus with the paranasal sinus of interest. The route of the fistula may be from the orbit to a frontal sinus, an ethmoid sinus or a maxillary sinus. The route may be subconjuctival from the orbit and through a wall of the frontal, ethmoid or maxilla bone, as the case may be. The fistula may be between the nasolacrimal duct and either a maxillary sinus or an ethmoid sinus. The location and the nasolacrimal duct where the fistula is formed may be in a top part of the nasolacrimal duct known as the lacrimal sac or may be in a location in the nasolacrimal duct below the lacrimal sac. Although not generally a preferred route, the fistula may be to the sphenoid sinus, such as subconjunctivally from the orbit and through a wall of the sphenoid bone to the sphenoid sinus. The fistula may be a durably patent fistula, for example when access to the paranasal sinus is desired over an extended period of time. The fistula may be more temporary in nature and formed to perform a single procedure after which it is desired that the fistula will quickly repair and close.

The fistula involved with methods of the invention may be formed by accessing a location in the lacrimal apparatus where the proximal end of the fistula is to be located, and the fistula is then formed through tissue into the target paranasal sinus. The location in the nasolacrimal duct may be accessed through the nasolacrimal duct, such as when the location where the fistula is to be formed is located in the nasolacrimal duct. The location in the lacrimal apparatus (e.g., lacrimal sac portion of nasolacrimal duct) may be accessed through a canaliculus. When the location where the fistula will be formed is in the orbit, access may be directly to the orbit.

When a method involves a treatment formulation (also referred to as a treatment composition) the treatment formulation may be a drug formulation (also referred to as a drug composition), for example for treatment of sinusitis or some other condition. Such a drug formulation may include one or more than one drug. Some example drugs that may be included in such a drug formulation include anti-inflammatories, antimicrobials, analgesics, mucolytics, antivirals, decongestants, steroids, antihistamines, antibiotics and antifungals. Such a treatment formulation may be an irrigation fluid, for irrigating the paranasal sinus.

Some specific methods of the invention involving a fistula between a lacrimal apparatus of a human and paranasal sinus are summarized below.

A third aspect of the invention is provided by a method for providing access to a paranasal sinus of the human to permit performance of medical treatments or procedures in the paranasal sinus over an extended time. The method comprises creating a surgically formed, durably patent fistula between the lacrimal apparatus of the human and the paranasal sinus.

A number feature refinements and additional features are applicable to the third aspect of the invention. These feature refinements and additional features may be used individually or in any combination. As such, each of the following features may be, but are not required to be, used with any other feature or combination of the third aspect or any other aspects of the invention.

One or more techniques may be used to help maintain durable patency of the fistula for an extended period of time. One technique for imparting durable patency is to, during the creating, surgically form the fistula with a relatively large diameter, and preferably with a clean cut to form the fistula. Such large diameter openings of clean cut tissue are highly resistant to natural repair mechanisms and such a fistula may remain open for a significant amount of time, which may essentially be permanent. The fistula may be formed with a diameter of at least 2 millimeters, or at least 3 millimeters. The fistula may be not greater than 6 millimeters, not greater than 5 millimeters, not greater than 4 millimeters or not greater than 3.5 millimeters. Another technique for imparting durable patency to the fistula comprises disposing through the fistula an implant device. The implant device occupies space within the fistula and prevents tissue from repairing and closing the fistula. The implant device may comprise an internal passage extending across the entire length of the fistula. A conduit of the implant device made to be disposed through the fistula to maintain patency. The implant device may be according to the first aspect of the invention. The implant device may be other than according to the first aspect of the invention. The implant device may be implanted using a surgical tool of a second aspect of the invention. The fistula may be formed using a surgical tool according to the second aspect of the invention. Forming the fistula may include formation of the fistula using one surgical tool and implanting the implant device with a different surgical tool. The fistula may be dilated between initial formation of the fistula and implantation of the implant device. One or more procedures may be aided by the use of a guide wire extending through the fistula. For example, implantation of the implant device may involve the use of such a guide wire. As another example, dilation of the fistula may involve the use of such a guide wire. Another technique that may be used to impart durable patency to the fistula comprises mechanical treatment of tissue adjacent to fistula to inhibit tissue repair and closing of the fistula. One mechanical treatment technique may be over-sewing tissue adjacent to the fistula. Another mechanical treatment technique may be stapling tissue adjacent to the fistula. Another technique for imparting durable patency to the fistula is treating tissue adjacent the fistula with a substance (e.g., a drug) effective to inhibit natural repair of the fistula. The substance may include an antigranulation agent or an anti-scarring agent. The substance may comprise a steroid. The substance may comprise Mitomycin C.

The method may include performing a procedure involving introduction of a treatment formulation through the fistula into the paranasal sinus. Such a treatment formulation may include a drug formulation. Such a treatment formulation may include an irrigation fluid for irrigating the paranasal sinus. The method may comprise a procedure involving removal of fluid from a paranasal sinus. Such removal may be effected by gravity drainage when the fistula is to a location in the lacrimal apparatus at a lower elevation than the paranasal sinus (e.g., fistula from frontal sinus to orbit). Introducing a treatment formulation into the paranasal sinus or removing fluid from the paranasal sinus, as the case may be, may be performed through a hollow member disposed through the fistula. Treatment formulation may be injected into the paranasal sinus from such a hollow member and fluid may be removed by aspiration from the paranasal sinus through such a hollow member. Such a hollow member may be disposed through the fistula contemporaneously with formation of the fistula. The hollow member may be a hollow member of a surgical tool according to the second aspect of the invention. The invention may comprise performing a procedure at a later time not contemporaneous with forming the fistula. The method may comprise performing a treatment comprising administering a treatment formulation to the vicinity of the eye to flow from the lacrimal apparatus through the fistula into the paranasal sinus. The treatment formulation may be administered in the form of eye drops. The treatment composition may be an ophthalmic composition.

A fourth aspect of the invention is provided by a method for delivering a treatment formulation to a paranasal sinus of a human. The method comprises administering the treatment formulation for delivery to the paranasal sinus through a fistula formed between the lacrimal apparatus of a human and a paranasal sinus.

A number of feature refinements and additional features are applicable to the fourth aspect of the invention. These feature refinements and additional features may be used individually or in any combination. As such each of the following features may be, but are not required to be, used with any other features or combination of the fourth aspect or any other aspects of the invention.

The administering may comprise injecting the treatment formulation into the paranasal sinus from the hollow member disposed through the fistula. Such a hollow member may be a hollow needle or cannula. The fistula may be a surgically formed, durably patent fistula. The fistula may be not durably patent. The hollow member may be disposed through the fistula for the purpose of delivering the treatment composition, after which the hollow member may be removed to permit the fistula to repair and close.

The administering may comprise administering the treatment formulation to the vicinity of an eye to flow from the lacrimal apparatus through the fistula and into the paranasal sinus. The treatment composition may be administered in the form of eye drops. The eye drops may be an ophthalmic composition.

A fifth aspect of the invention is provided by a method for performing a medical procedure in a paranasal sinus. The method comprises aspirating fluid from or injecting fluid into the paranasal sinus through a conduit of a medical device while the conduit is disposed through the fistula between the lacrimal apparatus and the paranasal sinus.

A number feature refinements and additional features are applicable to the fifth aspect of the invention. These feature refinements and additional features may be used individually or in any combination. As such, each of the following features may be, but are not required to be used with any other feature or combination features of the fifth aspect or any other aspects of the invention.

The conduit may be a conduit of an implant device. The implant device may be according to the first aspect of the invention. The implant device may be other than as according to the first aspect of the invention. The conduit may comprise a hollow member disposed through the fistula with the tip of the hollow member disposed within the paranasal sinus. Such a hollow member may be, for example, a hollow needle or a cannula. The fluid may comprise a treatment formulation.

A sixth aspect of the invention is provided by a method for treating a paranasal sinus of a human. The method comprises transmitting lacrimal fluid from the lacrimal apparatus through a surgically formed, durably patent fistula between the lacrimal apparatus of the human and a paranasal sinus.

A number of feature refinements and additional features are applicable to the sixth aspect of the invention. These feature refinements and additional features may be used individually or in any combination. As such each of the following features may be, but are not required to be, used with any other feature or combination of features of the sixth aspect or any other aspects of the invention.

Lacrimal fluid (tears) have significant therapeutic properties and providing a supply of lacrimal fluid to a paranasal sinus may have a beneficial effect concerning sinus conditions, such as sinusitis. The fistula may be maintained durably patent by any appropriate technique or techniques, such as those discussed previously. The fistula may be maintained as durably patent by an implant device with an internal passage providing fluid communication between the lacrimal apparatus and the paranasal sinus for conducting lacrimal fluid from the lacrimal apparatus to the paranasal sinus. The implant device may be according to the first aspect of the invention. The fistula may be between locations in the lacrimal apparatus and a paranasal sinus as previously described. One preferred fistula route is between the orbit and an ethmoid sinus. Another preferred fistula route is between the orbit and a maxillary sinus.

A seventh aspect of the invention is provided by a kit comprising multiple surgical tools. The kit includes a first surgical tool designed for initially forming a fistula and a second surgical tool including an implant device and designed for implantation of an implant device in a fistula after the fistula has already been formed to a desired size.

A number of feature refinements and additional features are applicable to the seventh aspect of the invention. These feature refinements and additional features may be used individually or in any combination. As such each of the following features may be, but are not required to be, used with any other feature or combination of features of the seventh aspect or any other aspects of the invention.

The kit may include a third surgical tool designed to dilate a fistula as initially formed using the first surgical tool. The kit may include a guide wire that may be used to guide tools to and through the fistula. The second surgical tool may be a surgical tool according to the second aspect of the invention. The implant device of the second surgical tool may be according to the first aspect of the invention. The implant device of the second surgical tool may be not according to the first aspect of the invention.

BRIEF DESCRIPTION OF THE DRAWINGS

FIG. 11 is an illustration of various head configurations for an implant device.

FIG. 25 is an illustration showing use of a surgical tool to dilate a fistula following initial formation of the fistula during a surgical procedure.

DETAILED DESCRIPTION

Figure 1:
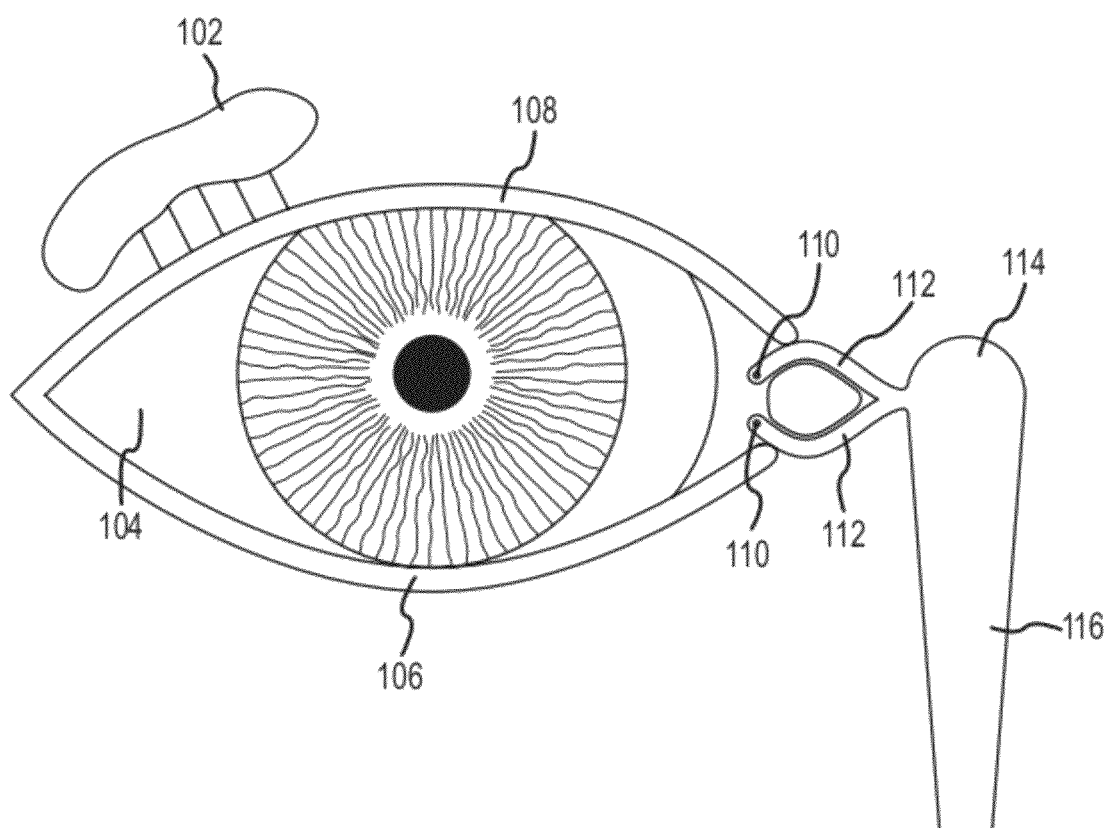
FIG. 1 is an illustration showing components of the lacrimal apparatus.

The terms "lacrimal apparatus" and "lacrimal system" are used interchangeably herein to refer to the collection of physiological components that accomplish the production and secretion of lacrimal fluid to lubricate the eyeball, containment of lacrimal fluid in a reservoir of lacrimal fluid in the orbit and drainage of lacrimal fluid from the orbit to the nasal cavity. The lacrimal apparatus includes the lacrimal glands, the tear drainage system and the reservoir of lacrimal fluid located between the lacrimal glands and the tear drainage system. The reservoir of lacrimal fluid includes the eyelid margins and the conjunctival sac (and including the pool of tears in the lower conjunctival cul-de-sac that is sometimes referred to as the lacrimal lake). The tear drainage system includes the puncta, canaliculi and nasolacrimal duct (including the so-called lacrimal sac located at the top of the nasolacrimal duct) through which excess tears drain to Hasner's valve and into the nasal cavity. FIG. 1 shows generally the lacrimal apparatus. Lacrimal fluid is produced and secreted from lacrimal glands 102 to lubricate the surface of the eyeball 104 disposed within the orbit. Lacrimal fluid forms a coating over the eyeball 104 and is generally contained within the conjunctival sac (the space between the lower eyelid 106, upper eyelid 108 and eyeball 104 that is lined by the conjunctiva). Excess lacrimal fluid is conducted to the vicinity of the medial canthus (medial corner of the eye) and drains through the lacrimal puncta 110 into the lacrimal canaliculi 112 and into the lacrimal sac 114 of the nasolacrimal duct 116. The lacrimal fluid then drains from the nasolacrimal duct 116 through Hasner's valve and into the nasal cavity.

Figure 2:
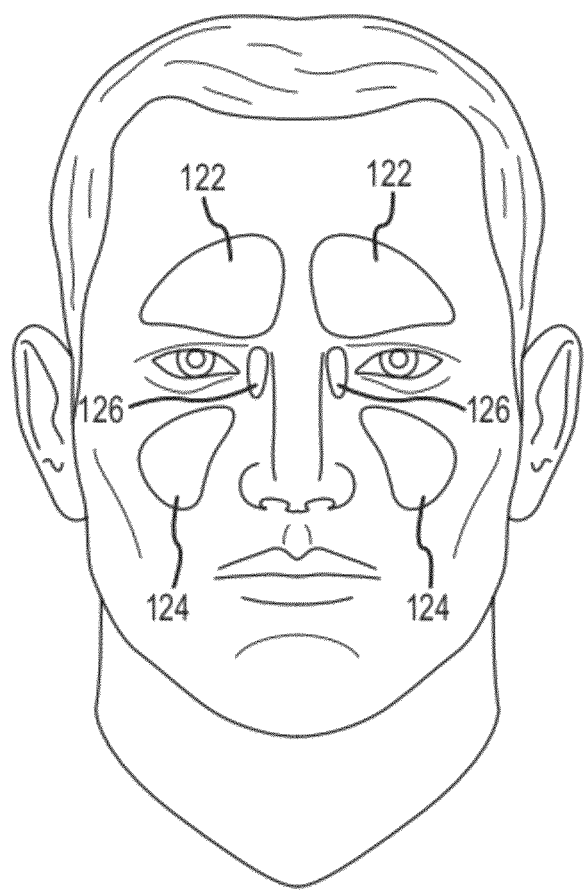
FIG. 2 is an illustration showing general locations of paranasal sinuses.
Figure 3:
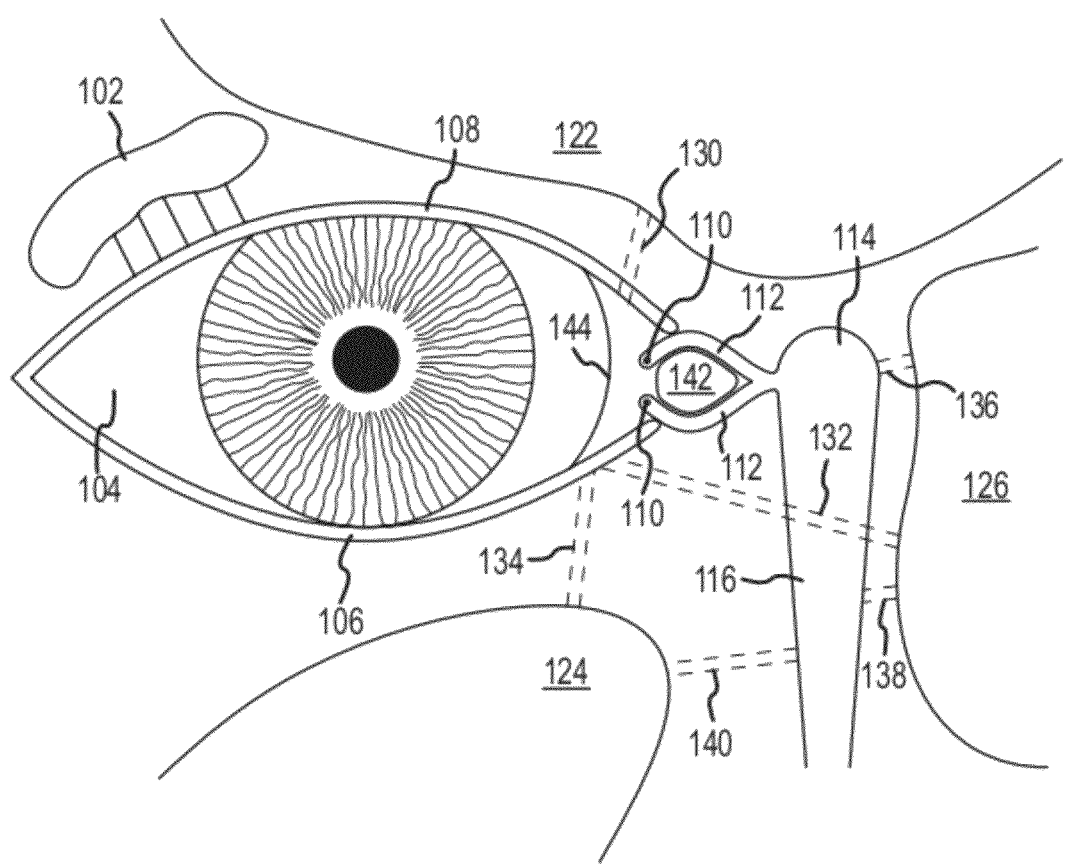
FIG. 3 is an illustration showing some example routes for fistulas between the lacrimal apparatus and the paranasal sinuses.
Figure 4:
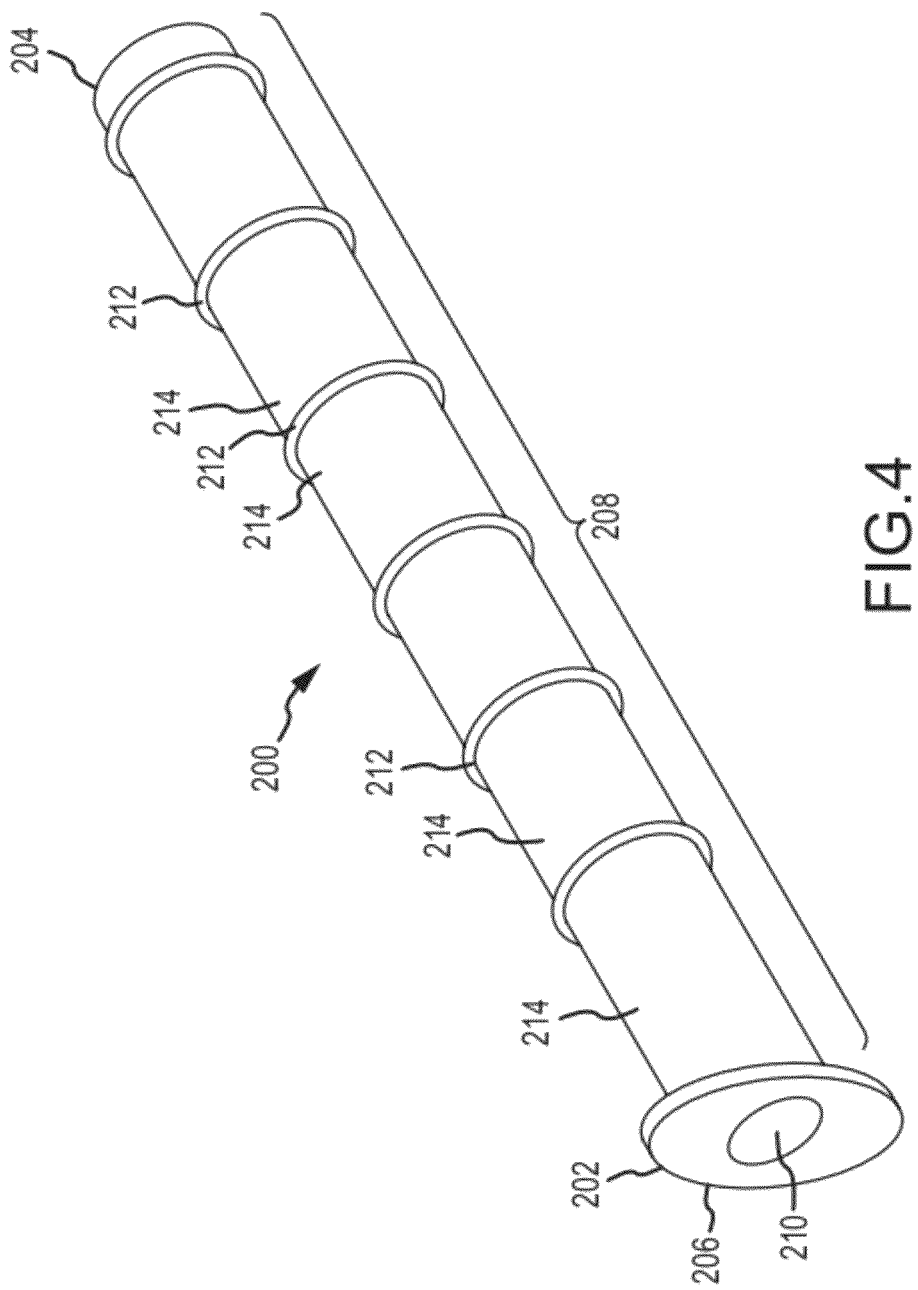
FIG. 4 is perspective view of one embodiment of an implant device.
Figure 5:
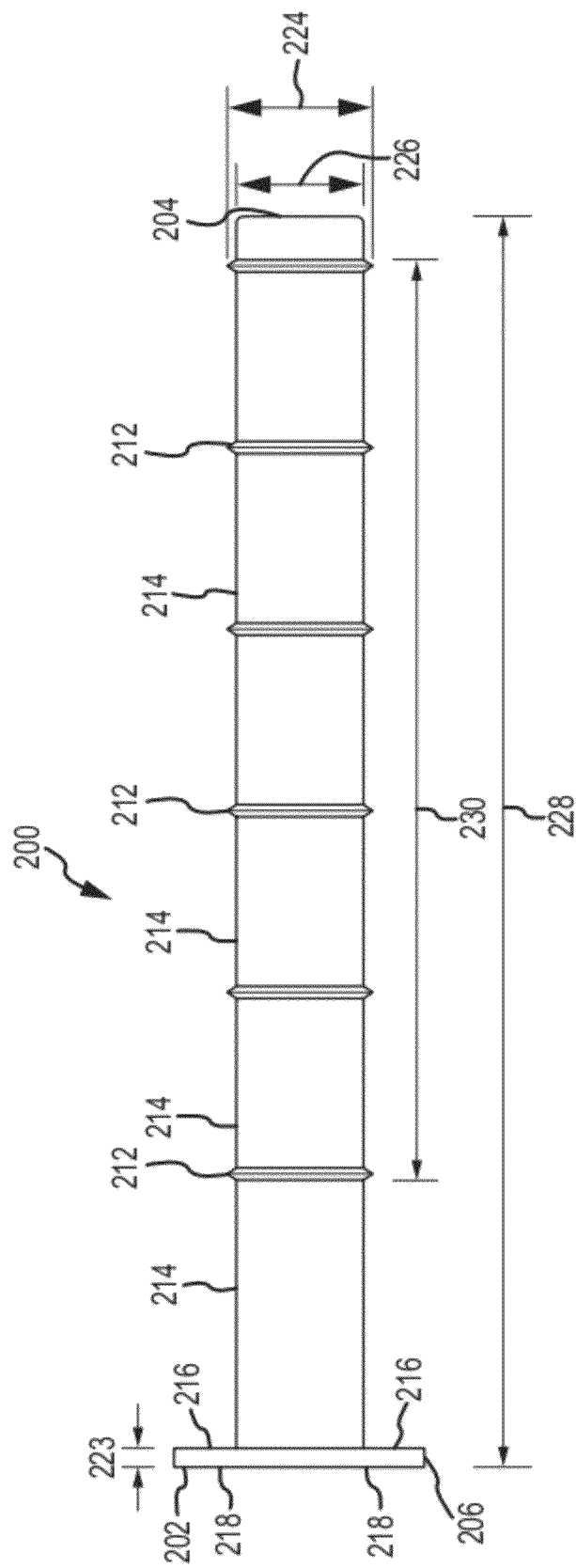
FIG. 5 is a side view of the same embodiment of an implant device as shown in FIG. 4.
Figure 6:
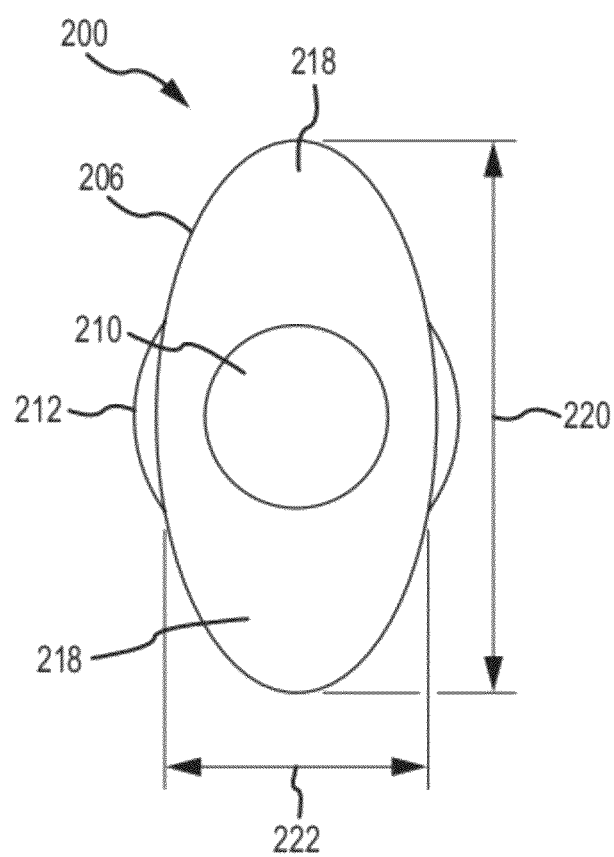
FIG. 6 is an end view of the same embodiment of an implant device as show in FIG. 4.
Figure 7:
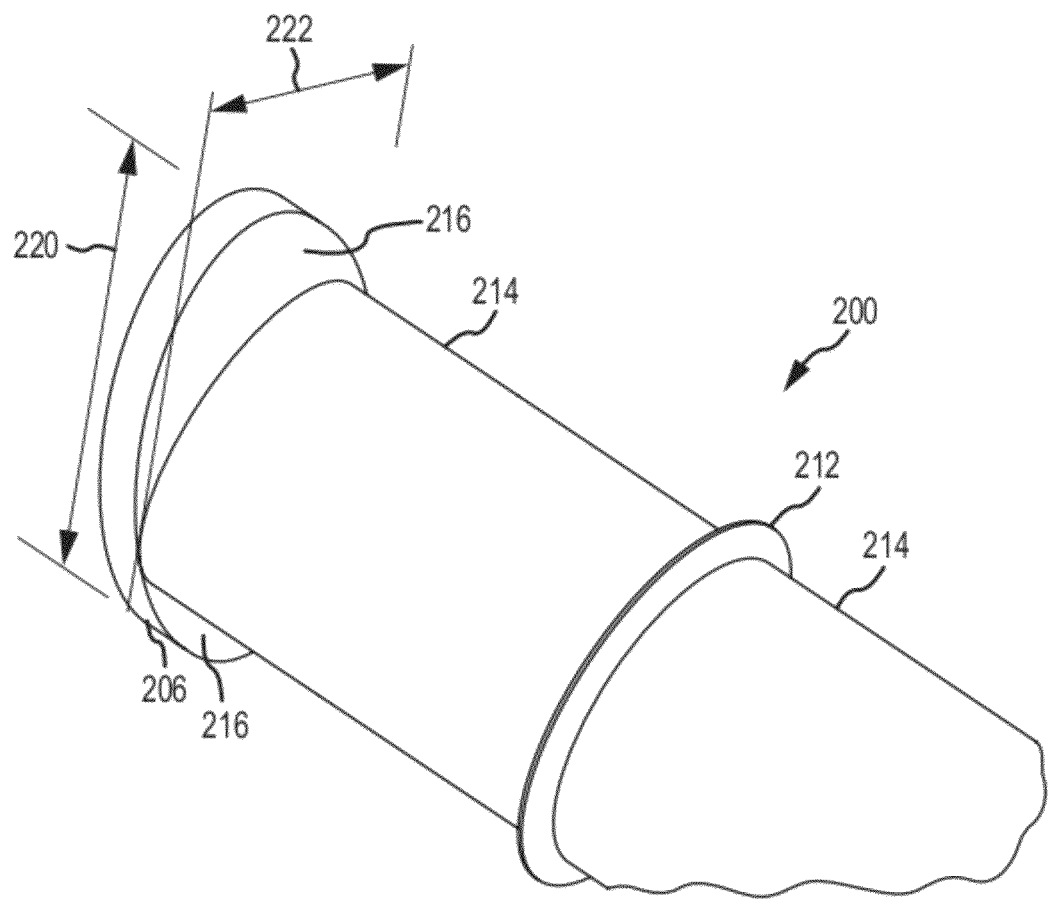
FIG. 7 is a partial perspective view of the same embodiment of an implant device as shown in FIG. 4.

As used herein, a fistula between the lacrimal apparatus and a paranasal sinus refers to an artificially-created passage that fluidly connects the lacrimal apparatus with the paranasal sinus. The paranasal sinuses include the frontal sinuses, maxillary sinuses, ethmoid sinuses and sphenoid sinuses, which are cavities contained within frontal, maxilla, ethmoid and sphenoid bones, respectively. The paranasal sinuses drain into the nasal cavity. FIG. 2 is a schematic of a human head showing generally the locations of the frontal sinuses 122, the maxillary sinuses 124 and the ethmoid sinuses 126. The sphenoid sinuses (not shown) are located generally behind the ethmoid sinuses 126. FIG. 3 shows generally some possible routes for a fistula between the lacrimal system and a paranasal sinus. Reference numerals indicate the same features as shown in FIGS. 1 and 2, except as noted. FIG. 3 shows the general proximity of the frontal sinus 122, maxillary sinus 124 and ethmoid sinus 126 relative to features of the lacrimal apparatus. Some example fistula routes are shown in FIG. 3 by dashed lines. A first example fistula route 130 is from the orbit to the frontal sinus. A second example fistula route 132 is from the orbit to the ethmoid sinus 126. A third example fistula route 134 is from the orbit to the maxillary sinus 124. A fourth example fistula route 136 is from the lacrimal sac 114 at the top of the nasolacrimal duct 116 to the ethmoid sinus 126. A fifth example fistula route 138 is from the nasolacrimal duct 116 at a location below the lacrimal sac 114 to the ethmoid sinus 126. A sixth example fistula route 140 is from the nasolacrimal duct 116 at a location below the lacrimal sac 114 to the maxillary sinus 124. The example fistula routes shown in FIG. 3 are for purposes of general illustration only and not show precise locations where a fistula might be formed to connect a part of the lacrimal apparatus with the corresponding paranasal sinus. Although not shown in FIG. 3, example fistula routes to the sphenoid sinus include from the orbit to the sphenoid sinus and from the nasolacrimal duct 116 to the sphenoid sinus. Forming a fistula to connect to the sphenoid sinuses is generally not as preferred as forming a fistula to connect to the ethmoid sinus, for example because it is generally more convenient and direct to connect with the ethmoid sinus. Also, forming a fistula to either the ethmoid sinus 126 or the maxillary sinus 124 is generally preferred to forming a fistula to the frontal sinus 122, with one reason being that a fistula between the lacrimal system and either the ethmoid sinus 126 or the maxillary sinus 124 may be formed in a way to obtain the benefit of gravity to assist drainage of lacrimal fluid from the lacrimal system into the corresponding paranasal sinus through the fistula. The frontal sinus is located generally above the orbit and will not benefit in the same way from gravity drainage of lacrimal fluid into the paranasal sinus. However, gravity drainage may beneficially assist drainage of fluid from the frontal sinus.

With continued reference to FIG. 3, the first, second and third example fistula routes 130, 132 and 134 are subconjuctival routes that penetrate the conjunctiva to directly connect the lacrimal fluid reservoir within the conjunctival sac to the corresponding paranasal sinus. A fistula along such a subconjunctival route may be surgically formed by a surgical tool piercing through the conjunctiva and the adjacent wall of the bone in which is disposed the corresponding paranasal sinus. For example, for the first example fistula route 130, the fistula would pass subconjunctivally from the orbit and through a wall of the frontal bone into the frontal sinus 122. For example, a fistula following second example fistula route 132 would pass subconjuctivally from the orbit and through a wall of the ethmoid bone into the ethmoid sinus 126. For example, a fistula following the third example fistula route 134 would pass subconjuctivally from the orbit through a wall of the maxilla bone into the maxillary sinus 124. Subconjuctival routes for a fistula such as those of the first, second and third example fistula routes 130, 132 and 134 are generally preferred as being formed at locations that are relatively easy to access. In a preferred implementation of the first, second and third example fistula routes 130, 132 and 134, the proximal end of the fistula opening into the orbit is located between the lacrimal caruncle 142 and the plica semilunaris 144, shown in FIG. 3.

Continuing with reference to FIG. 3, a fistula at the fourth, fifth or sixth example fistula routes 136, 138 and 140 will have a proximal end opening into a location within the nasolacrimal duct 116. Formation of a fistula in such a location requires insertion of a surgical tool into the lacrimal drainage system, such as through the puncta 110 and canaliculi 112 to access the nasolacrimal duct 116 or through the nose to access the nasolacrimal duct 116. For example, a fistula at the fourth example fistula route 136 may be formed by a piercing instrument (e.g., a trocar or trocar/cannula assembly) inserted into one of the puncta 110, through one of the canaliculi 112 and across the lacrimal sac 114 to pierce a hole at the location of the fourth example fistula route 136. As another example, a fistula may be formed at one of the fourth, fifth and sixth example fistula routes 136, 138 and 140 using a guide wire inserted into one of the puncta 110, through one of the canaliculi 112, into the lacrimal sac 114 and downward through the nasolacrimal duct 116. The guide wire may be used to engage a surgical tool and to guide the surgical tool from the nose through Hasner's valve (not shown) and to the appropriate location within the nasolacrimal duct 116 to permit performance of a surgical operation at that location to form the desired fistula.

FIGS. 4-7 show one embodiment of an implant device. As shown in FIGS. 4-7, an implant device 200 has a proximal end 202 and a distal end 204 located on opposite longitudinal ends of the implant device 200. The implant device 200 includes a head 206 at the proximal end 202 and a conduit 208 extending from the head 206 to the distal end 204. An internal passage 210 extends from the proximal end 202 to the distal end 204, passing through the head 206 and the conduit 208. The internal passage 210 opens at the proximal end 202 and the distal end 204, thereby providing a passage through the entire longitudinal length of the implant device 200. The internal passage 210 of the embodiment shown in FIG. 4 has a cylindrical shape with a uniform circular cross-section (transverse to the length of the implant device 200), and the width of the internal passage is equal to the diameter of the circle of the cross-section and is uniform along the length of the implant device 200. The length of the implant device 200 is the minimum distance longitudinally along the implant device 200 between the proximal end 202 and the distal end 204, and will typically be equal to the distance along an axis of the internal passage 210 from the proximal end 202 to the distal end 204. The implant device 200 includes multiple anchor protrusions 212 on an exterior of the conduit 208. In the embodiment shown in FIGS. 4-7, the anchor protrusions 212 are in the form of spaced circumferential ridges that each extends around the entire circumference of the conduit 208. Adjacent the circumferential ridges of the anchor protrusions 212 are areas of recess 214 on the exterior of the conduit 208.

With continued reference to FIGS. 4-7, when the implant device is implanted to fluidly connect the lacrimal apparatus to a paranasal sinus through a fistula, the head 206 is disposed in the lacrimal apparatus and the proximal end 202 is disposed in the paranasal sinus, and with at least a portion of the conduit 208 disposed through the fistula with at least one, and preferably more than one, of the anchor protrusions 212 engaging tissue within the fistula to anchor the implant device 200. When implanted in this manner, the internal passage 210 opens into the lacrimal apparatus at the proximal end 202 and into the paranasal sinus at the distal end 204. The head 206 has a flanged tissue engagement surface 216 on a side of the head 206 disposed toward the conduit 208, and which flanged tissue engagement surface 216 is advantageously configured to engage tissue adjacent the proximal end of fistula and to prevent the proximal end 202 of the implant device 200 from migrating into the fistula following implantation. On the side of the head 206 opposite the flanged tissue engagement surface 216 is a face surface 218 of the head 206, which face surface 218 is disposed away from tissue engaged by the flanged tissue engagement surface 216 when the implant device is implanted. The head 206 has a first dimension 220 and a second dimension 222 on both the flanged tissue engagement surface 216 and the face surface 218. The first dimension 220 is the length of the respective surface and the second dimension is the width of the respective surface. Such length and width dimensions may also be referred to as major and minor dimensions. The first dimension 220 of a surface 216 or 218 corresponds to the maximum separation distance between points on the outer edge of the surface, and the second dimension 222 of the surface 216 or 218 corresponds to the maximum separation distance between points on the outer edge of the surface that are on a line transverse to the first dimension. Conveniently, the face surface 218 and the flanged tissue engagement surface 216 may be made with corresponding outer edges, so that the opposing surfaces 216 and 218 have substantially equal length and width dimensions, although such is not required. The first dimension 220 and the second dimension 222 may be referred to generally as the length and width, respectively, of the head 206 when the surfaces 216 and 218 have corresponding shapes, as is the case for the embodiment shown in FIGS. 4-7. When the surfaces 216 and 218 do not have corresponding shapes, the length and width dimensions of the head will be different from one or more of the length and width dimensions of the surfaces 216 and 218. The head 206 has a depth dimension 223 between surfaces 216 and 218. The depth dimension 223 should preferably be kept to a small value so that the head 206 will have a low profile adjacent the proximal end of the fistula when the implant device 200 is implanted with the flanged tissue engagement surface engaging tissue adjacent the proximal end of the fistula.

With continued reference to FIGS. 4-7, the conduit 208 has a first exterior width 224 that is a maximum exterior width of the conduit 208 as defined by the maximum extents of the anchor protrusions 212 transverse to the length of the conduit 208. The conduit 208 has a second exterior width 226 that is a minimum exterior width of the conduit 208 defined between the most recessed portions of the areas of recess 214. In the embodiment shown in FIGS. 4-7, the height of the anchor protrusions 212 is equal to one-half the difference between the first exterior width 224 and the second exterior width 226 of the conduit 208. In the configuration of the head 206 shown in FIG. 4-7, the first dimension 220 of the head is larger than both the first exterior width 224 and the second exterior width 226 of the conduit 208, while the second dimension 222 of the head is approximately equal to the second exterior width 224 of the conduit 208.

With continued reference to FIGS. 4-7, the anchor protrusions 212 are in the form of circumferential ridges having a width that is at a maximum at the bottom of the ridges located adjacent the areas of recess 214, and which width tapers to a minimum at the top of the ridges 212 located away from the recess areas 214. Other configurations for anchor protrusions are possible, and all anchor protrusions on an implant device need not be of the same size, geometry or height. Likewise, areas of recess may have varying configurations, and not all recesses on an implant device need to be the same size or configuration. The implant device 200 has a length 228 including the depth 223 of the head 206 and the length of the conduit 208. The anchor protrusions 212 are on a longitudinal portion 230 of the conduit 208.

Figure 8:
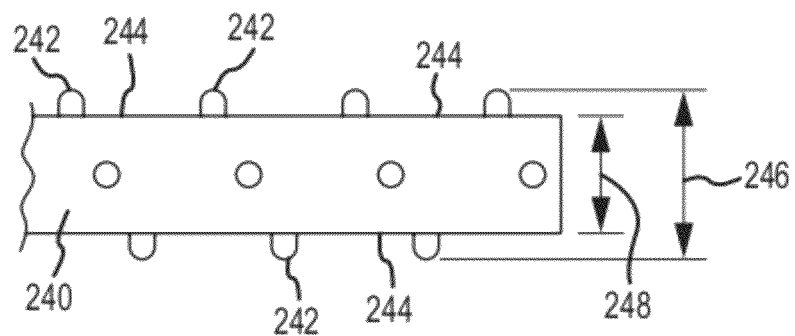
FIG. 8 is a partial side view of an embodiment of an implant device.
Figure 9:
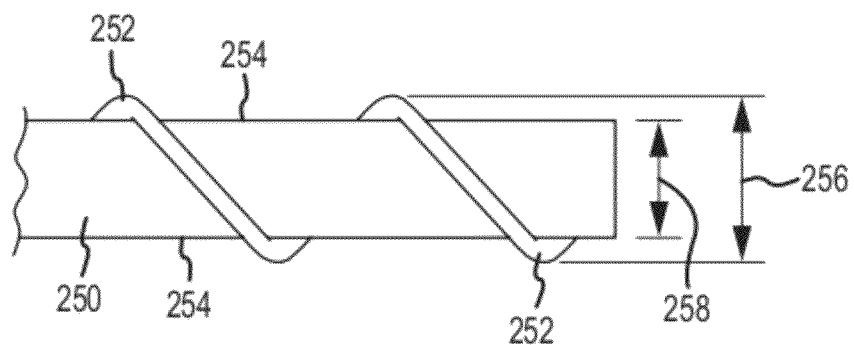
FIG. 9 is a partial side view of an embodiment of an implant device.

Referring now to FIG. 8, an alternative embodiment is shown of a conduit 240 of an implant device having anchor protrusions 242 in the form of knobs, or buttons, and areas of recess 244 adjacent the anchor protrusions 242. The conduit 240 has a first exterior width 246 defined by the anchor protrusions 242 and a smaller, second exterior width 248 defined by the areas of recess 244. An example of another configuration for anchor protrusions is shown in FIG. 9. As shown in FIG. 9, a conduit 250 of an implant device has anchor protrusions 252 and areas of recess 254 on the exterior surface of the conduit 250. The anchor protrusions 252 are in the form of a continuous spiral ridge extending along a portion of the longitudinal length of the conduit 250. The conduit 250 has a first exterior width 256 defined by the anchor protrusions 254 and a smaller, second exterior width 258 defined by the areas of recess 254. As with the embodiments shown in FIGS. 4-7, the conduit embodiment shown in FIGS. 8 and 9 include a height of the anchor protrusions that is equal to one half the difference between the larger and smaller outer diameters of the respective conduits. As will be appreciated from the embodiments of FIGS. 8 and 9, the first exterior width is determined as the width of an envelope volume that contains the anchor protrusions.

Figure 10:
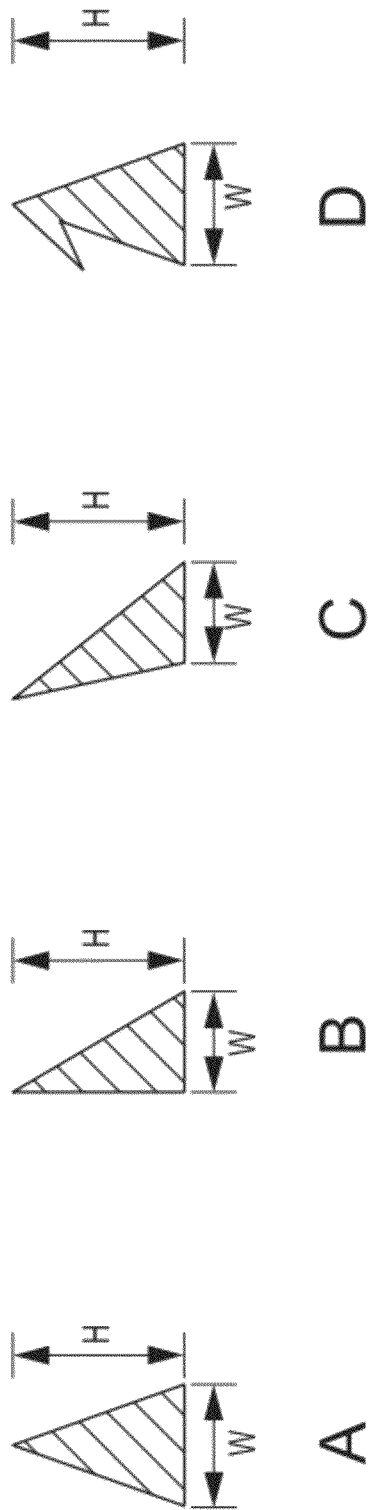
FIG. 10 is an illustration of cross-sections of various configurations for anchor protrusions for an implant device.

FIG. 10 shows examples of some shapes for anchor protrusions that include a tapering width in a direction from the base of the anchor protrusion toward a top of the anchor protrusion. FIG. 10 shows cross-sections of anchor protrusion configurations (designated A-D), each having a greater width at the base than at the top. The height (H) and base width (W) of the anchor protrusions are indicated in FIG. 10. The cross-sections shown in FIG. 10 may, for example, be across a ridge (e.g., circumferential ridge, spiral ridge), a knob protrusion or other anchor protrusion form. All of the anchor protrusion configurations A-D in FIG. 10 are shown with a leading side of the anchor protrusion on the right side and a trailing side on left side of the anchor protrusion. By leading side it is meant a side that enters the fistula first when a conduit containing the anchor protrusion is inserted into the fistula for implantation. By trailing side it is meant the side opposite the leading side and that enters the fistula after the leading side. As will be appreciated, forces applied to the anchor protrusions by tissue contacting the anchor protrusions during insertion into a fistula will impart stresses to the anchor protrusions and, to an extent as permitted by the material of construction of the anchor protrusion, such stresses will tend to deform the anchor protrusion in a direction toward the trailing side. Such deformation aids insertion, and is generally preferred to some degree. The different shapes of the configurations A-D affect the relative ease of insertion of a conduit into and removal of the conduit from a fistula. Configuration A is designed to be equally easy to insert and removable from a fistula while each of configurations B-D are designed to be more easy to insert into a fistula and more difficult to remove from the fistula. Configurations B and C are angled in a way to promote more easy insertion and more difficult removal from a fistula. Configuration D includes a hooked end to engage tissue on the trailing side to make removal from a fistula more difficult than insertion.

FIG. 11 shows some different example configurations (designated E-H) for a head for an implant device. For each head configuration, the length dimension (L) and width dimension (W) of the head configurations are shown. The heads of configurations E-H are shown on end showing the face surface (surface facing away from the fistula when implanted) and the opening of the internal passage at the proximal end of the implant device. For each of the head configurations E-H, the length and width of the face surface and the opposing flanged tissue engagement surface are the same. As shown in FIG. 11, head configuration E has a circular outer edge, and thus has equal length and width dimensions. Head configuration F has an elongated length dimension relative to width dimension, similar to that shown in the implant device embodiment described with reference to FIGS. 4-7. Head configuration G has an elongated length dimension relative to the width dimension, similar to configuration F, but for configuration G the internal passage opening at the proximal end of the implant device has an elliptical cross-section, rather than a circular cross-section as is the case for configurations E and F. Head configuration H has a crescent-shaped head with a significantly larger length dimension than width dimension. The internal passage for configuration H is also shown with an elliptical cross-section. Configurations F-H, with a larger length than width, are advantageously configured for use with fistulas opening into the orbit between the plica semilunaris and the lacrimal caruncle, with the length dimension of the head extending generally in a direction from the bottom of the orbit toward the top of the orbit next to the eyeball, and for configuration H with the concave side of the crescent disposed toward the eyeball and the convex side of the crescent disposed towards the lacrimal caruncle.

Figure 12:
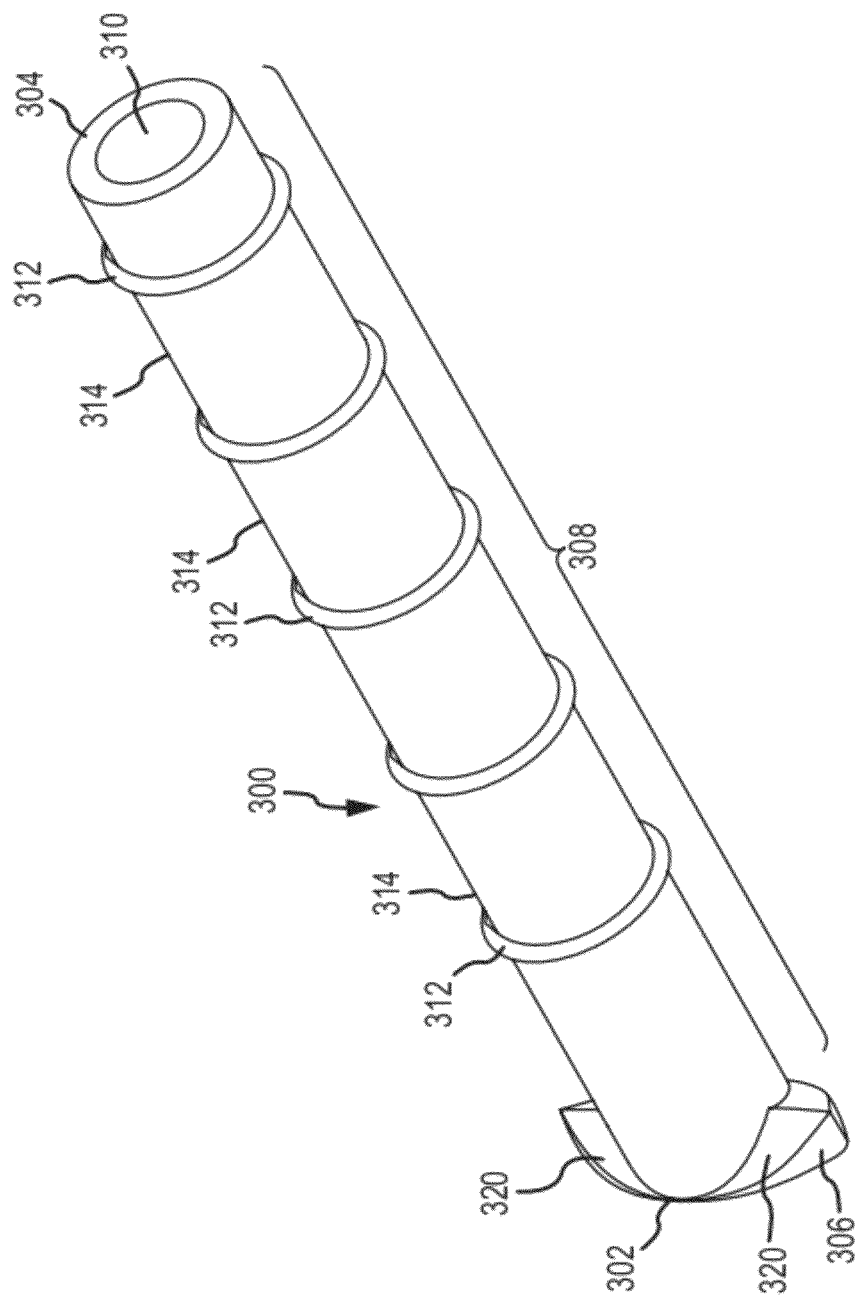
FIG. 12 is a perspective view of an embodiment of an implant device.
Figure 13:
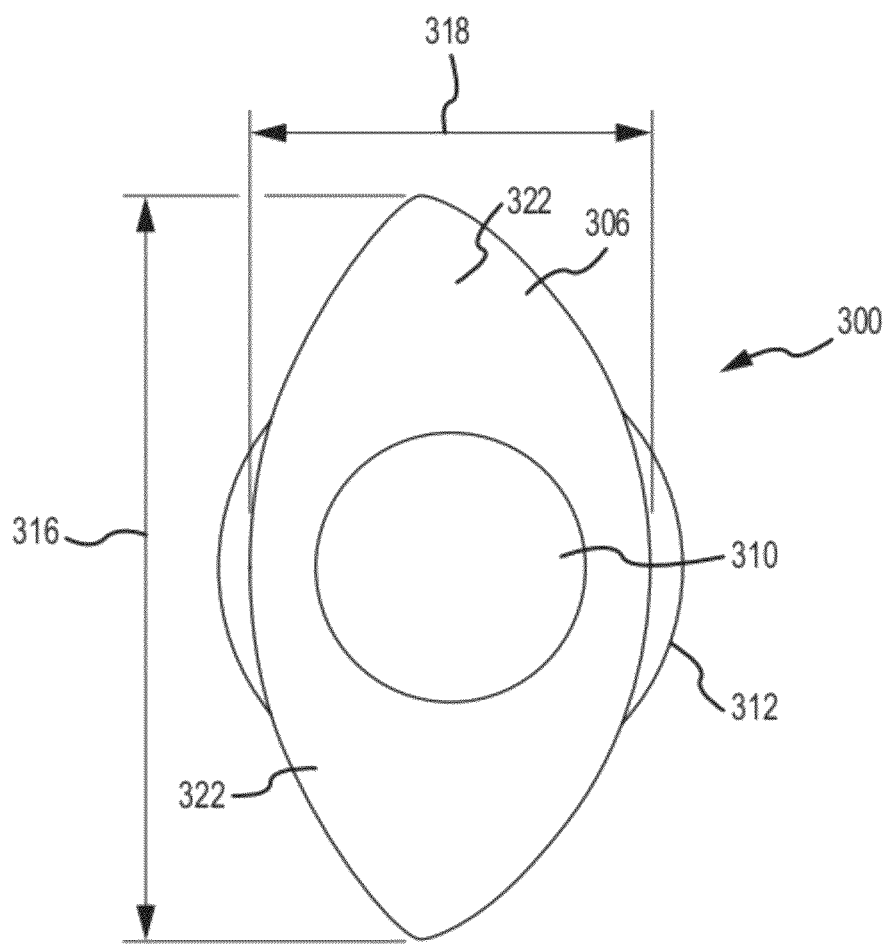
FIG. 13 is an end view of the same embodiment of an implant device shown in FIG. 12.

FIGS. 12 and 13 show another embodiment for an implant device. As shown in FIGS. 12 and 13, an implant device 300 has a proximal end 302 and a distal end 304, with a head 306 located at the distal end 304 and a conduit 308 extending from the head 306 to the distal end 304. The conduit 308 includes an internal passage 310 with a cylindrical shape and opening at the proximal end 302 and the distal end 304. The conduit 310 has an exterior surface including anchor protrusions 312, in the form of circumferential ridges with tapering width, and areas of recess 314 adjacent the anchor protrusions 312. The head 306 has an elongated shape with a significantly larger length dimension 316 than width dimension 318. As seen in FIG. 12, a flanged tissue engagement surface 320 has a beveled configuration (beveled halves extending from central line) to help seat against tissue in a manner to prevent rotation of the implant device 300 when implanted. The face surface 322 is a flat surface to provide a low profile to the head 306 when the implant device 300 is implanted. The configuration of the head 306 is well suited for placement between the plica semilunaris and lacrimal caruncle for use with a subconjunctival fistula route from the orbit where the opening of the fistula into the orbit is located between the plica semilunaris and the lacrimal caruncle. The length dimensions 316 and width dimension 318 represents the length and width of each of the face surface 322 and the flanged tissue engagement surface 320.

Figure 14:
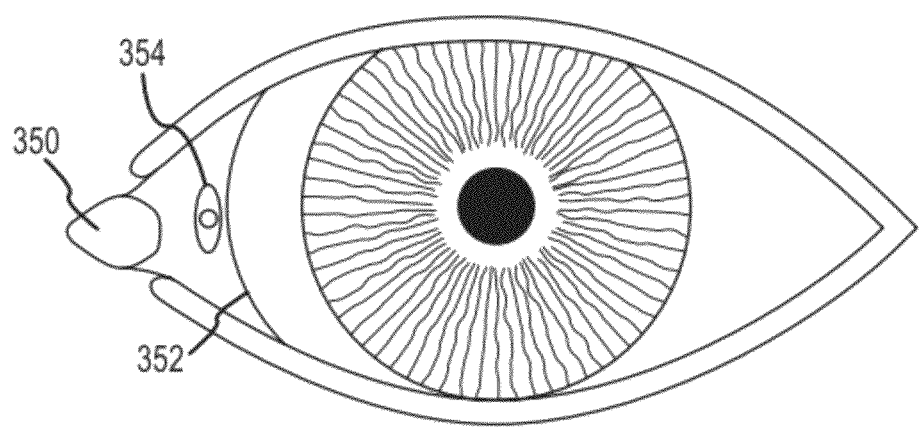
FIG. 14 is an illustration showing an embodiment for placement of an implant device between the lacrimal caruncle and plica semilunaris.

FIG. 14 shows an example of an implant device with a conduit passing through a fistula formed subconjunctivally between the lacrimal caruncle 350 and the plica semilunaris 352, and showing an example location for the head 354 of the implant device. The head 354 is shown with an elongated configuration, such as for example the head configuration shown in FIGS. 4-7, one of the head configurations F-H shown in FIG. 11 or the head configuration shown in FIGS. 12 and 13.

Figure 15:
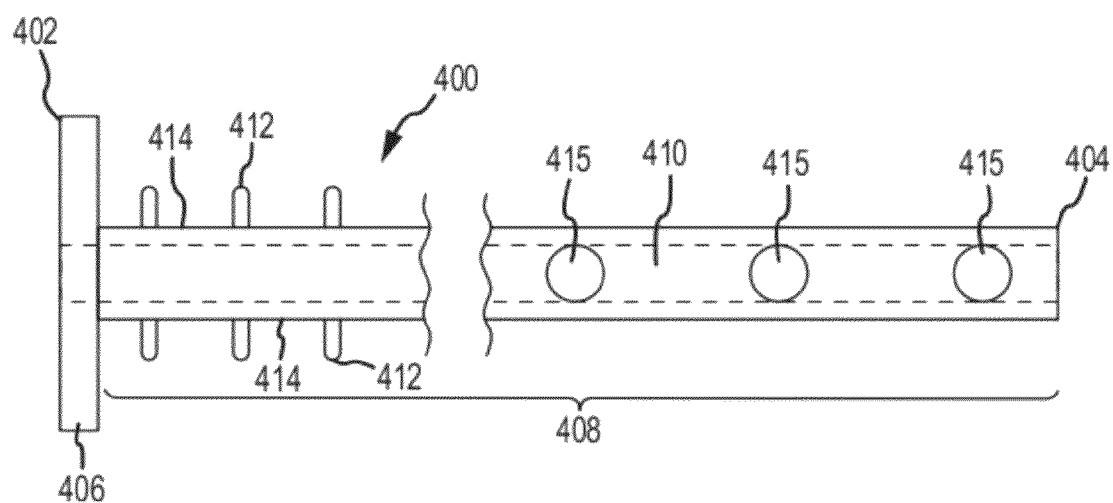
FIG. 15 is a side view of an embodiment of an implant device.

FIG. 15 shows another embodiment of an implant device. As shown in FIG. 15, an implant device 400 has a proximal end 402 and a distal end 404. The implant device 400 includes a head 406 at the proximal end 402 and a conduit 408 extending from the head 406 to the distal end 404. The conduit 408 has an exterior surface with anchor protrusions 412 and areas of recess 414 adjacent the anchor protrusions 412. An internal passage 410 (shown by dashed lines) extends from the proximal end 402 to the distal end 404. A distal longitudinal portion of the conduit 408 includes apertures 415 through the wall of the conduit 408 and providing fluid communication from the internal passage 410 to outside of the conduit 408. The apertures 415 provide a route for drug formulations, irrigation solutions or other treatment compositions to exit from the internal passage into different locations within a paranasal sinus when the implant device 400 is implanted. When the implant device 400 is implanted, at least one or more of the anchor protrusions 412 will be located within the fistula to engage tissue for anchoring and at least some, and preferably all, of the apertures 415 will be disposed beyond the distal end of the fistula inside of a paranasal cavity. The configuration shown in FIG. 15 is particularly advantageous for situations when the conduit 408 extends through multiple cavities of a paranasal sinus or when the conduit 408 extends from one paranasal sinus into another paranasal sinus. The embodiment shown in FIG. 15 does not include the anchor protrusions 412 on the longitudinal portion of the conduit 408 where the apertures 415 are disposed. As an alternative configuration, the longitudinal portion of the conduit 408 including the apertures 415 could include anchor protrusions, of the same configuration as those of the anchor protrusions 412 or of different configurations.

Figure 16:
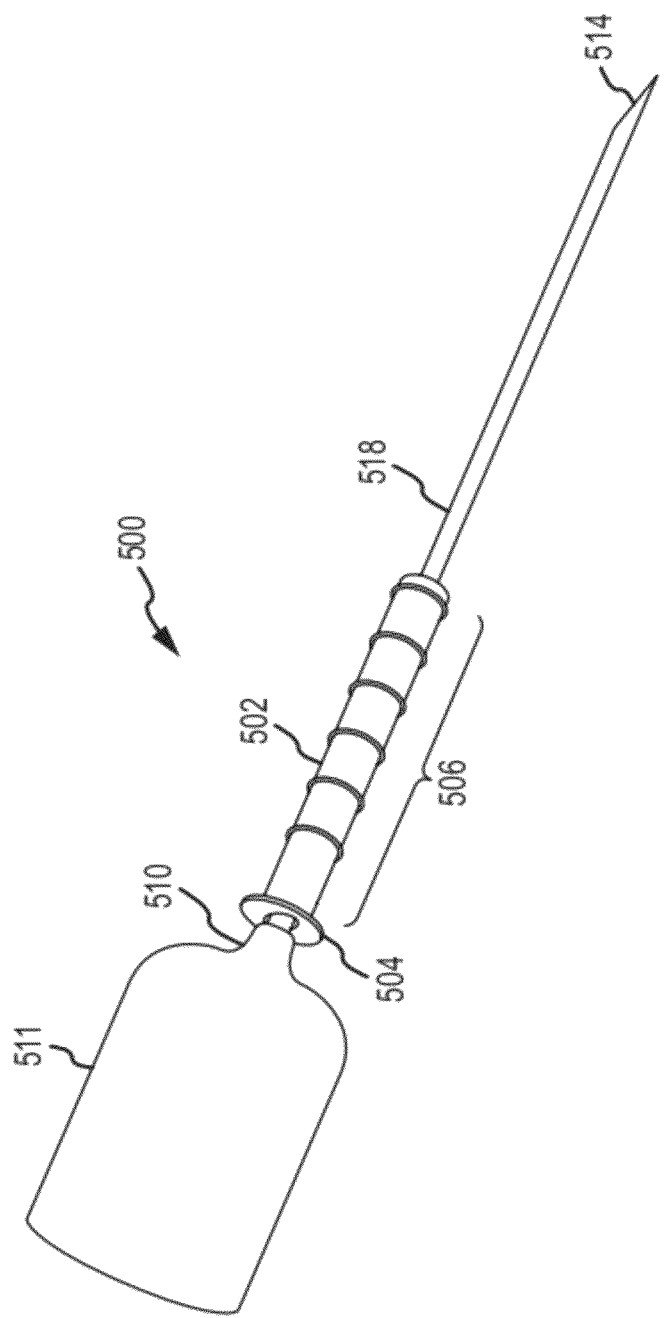
FIG. 16 is a perspective view of an embodiment of a surgical tool.

FIG. 16 shows one embodiment of a surgical tool. As shown in FIG. 16, a surgical tool 500 includes an implant device 502 having a head 504 and a conduit 506, for example as previously described with respect to any of the FIGS. 4-15. The implant device 502 is mounted on a carrier 510. The carrier 510 comprises a handle 511 adjacent a proximal end of the surgical tool 500. The carrier 510 includes a working member 512 connected to the handle 511. The working member 512 extends from the handle 511 through the internal passage of the implant device 502 and to a distal end of the surgical tool 500. At the distal end of the working member 512 is a distal tip 514. The handle 511 may be made of any convenient material of construction, for example plastic or metallic compositions. The working member 512 may be made for example of a medical-grade metallic composition, such as a medical-grade stainless steel. In general when a member is referred to herein as a "working member", the term indicates that the member is such that at least a portion of the member is designed for being disposed within or through a fistula when a tool containing the member is used, for example during formation of a fistula or during performance of some procedure in or through a fistula. Some examples of working members include various hollow members (e.g., hypodermic needles, cannulas) and various solid members (e.g., trocars, stylets, dilating members, implant delivery members). Such a working member may be disposed in or through the fistula in a manner that the member contacts tissue in the fistula or in a manner not to contact tissue in a fistula (e.g., inside of a passage of an implant device passing through the fistula).

With continued to reference to FIG. 16, the implant device 502 is mounted on the carrier 510 with the working member 512 disposed through the internal passage of the implant device 502. The width of the working member 512 disposed through the internal passage of the implant device 502 may advantageously be sized to be just smaller than the internal passage of the implant device for a close fit between them, provided that the fit is not so tight that the implant device 502 is difficult to slide down the working member 512 toward the distal tip 514.

Continuing to refer to FIG. 16, the surgical tool 500 may be used to form a fistula between the lacrimal system and a paranasal sinus and to facilitate implantation of the implant device 502 in the fistula. A surgeon may manipulate the surgical tool 500 by hand-grasping the handle 511. The surgeon may advance the distal tip 514 to a location within the lacrimal apparatus where the fistula is to be formed to a target paranasal sinus. The surgeon may then force the distal tip through tissue separating the lacrimal apparatus and the target paranasal sinus to form the fistula. With a leading portion of the working member 512 disposed through the fistula, a surgeon may slide the implant device 502 along the working member 512 toward the distal tip 514 until the implant device 502 is positioned for implantation with the conduit 506 disposed through the fistula and a flanged tissue engagement surface of the head 506 disposed against tissue adjacent the proximal end of the fistula in the lacrimal apparatus, or the carrier may continue to be advanced to push the conduit 506 into the fistula. After the implant device 502 is positioned for implantation, the surgeon may then manipulate the handle 504 to retract the working member 512 to withdraw the working member from the internal passage of the implant device 502 and to fully disengage the carrier 510 from the implant device 502, leaving the implant device 502 implanted with the conduit 506 extending through the fistula and into the paranasal sinus.

With continued reference to FIG. 16, the working member 512 may be a solid member (e.g., trocar, stylet) or may be a hollow member (e.g., a hollow needle, cutting cannula). If the working member 512 is a hollow member with an opening at the distal tip 514, then tissue will tend to be cored and collected in the hollow interior of the working member 512 when the surgical tool 500 is used to form a fistula. If the working member 512 is a solid member, then tissue coring should not occur. In many instances, it may be preferred to have the working member 512 be a solid member that does not core tissue, because the implant device may tend to be held more securely within a fistula formed without tissue coring. The surgical tool 500 shown in FIG. 16 is particularly well adapted for forming a fistula from the orbit subconjunctivally to a paranasal sinus, and particularly when the fistula is formed at a location in the orbit between the plica semilunaris and the lacrimal caruncle.

Figure 17:
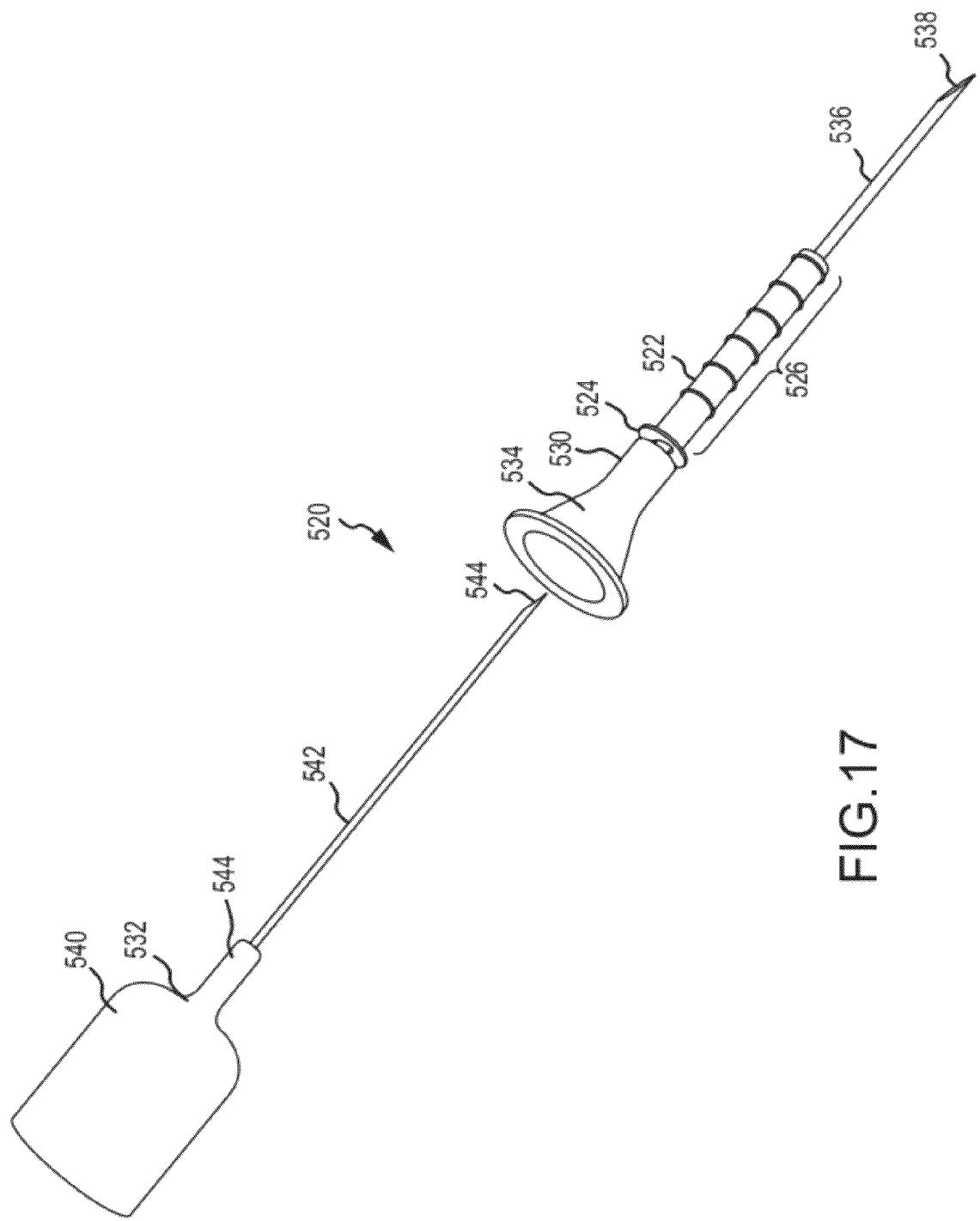
FIG. 17 is a perspective view of an embodiment of a surgical tool showing some components in exploded view.
Figure 18:
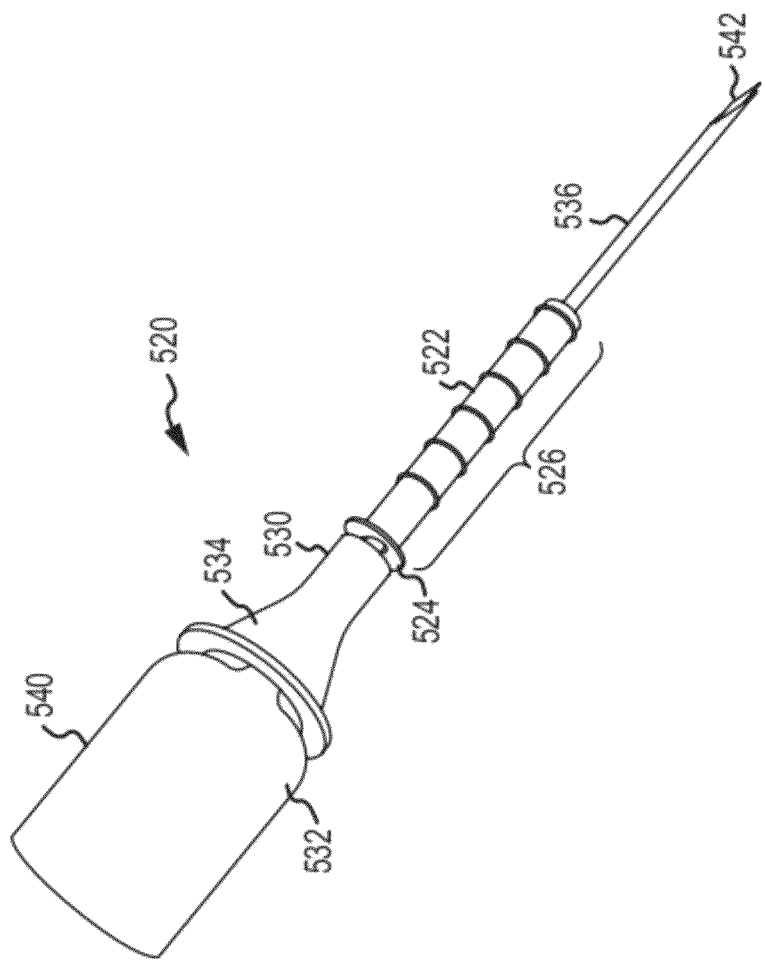
FIG. 18 is a perspective view of the same embodiment of a surgical tool shown in FIG. 17, showing the surgical tool fully assembled.

FIGS. 17 and 18 show another surgical tool. FIG. 17 shows an expanded view of some features of a surgical tool 520 and FIG. 18 shows the same surgical tool 520 as the surgical tool 520 appears fully assembled. As shown in FIG. 17, the surgical tool 520 includes an implant device 522 with a head 524 and a conduit 526, for example as described previously with respect to any of FIGS. 3-16. The surgical tool 520 includes a carrier with two pieces, a first carrier piece 530 and a second carrier piece 532. The first carrier piece 530 has a syringe hub 534 (e.g., for making a luer connection) and a hollow working member 536 (e.g., hollow needle, cannula) connected with the hub 534. The hollow working member 536 has a distal tip 538. The second carrier piece 532 has a handle 540 and a solid working member 542 (e.g., stylet, trocar) connected with the handle 540. The solid working member 542 has a distal tip 544. As assembled, the surgical tool 520 includes the solid working member 542 inserted through the interior of the hub 534 and through the hollow interior of the hollow working member 536. As assembled, the handle 540 of the second carrier piece 532 is disposed distal of the hub 534 with an engagement member 544 inserted into the interior of the hub 534. As will be appreciated, features of the hub 534 and/or the engagement member 544 and/or the handle 540 may contain keying and engagement features to align and/or permit detachable engagement of the first carrier piece and the second carrier piece when assembled. FIG. 18 shows the same surgical tool 520 as it appears fully assembled. As shown in FIG. 18, the first carrier piece 522 and the second carrier piece 532 are engaged with the solid working member 542 disposed through the hollow interior of the hollow working member 536.

With continued reference to FIGS. 17 and 18, the surgical tool 520 may be used to form a fistula between the lacrimal apparatus and a paranasal sinus. The distal tips 538 and 544 of the first and second carrier pieces 530 and 532 form a distal tip that will not significantly core tissue. A surgeon may grasp the handle 540 and advance the distal tip to a location in the lacrimal apparatus where the fistula is to be formed (e.g., in the orbit, in the nasolacrimal duct) and the distal tip may then be forced through tissue into a paranasal sinus to form the fistula to the target paranasal sinus. With a leading portion of the hollow working member 536 disposed through the fistula, the implant device 522 may be slid down the hollow working member 536 and into position for implantation with the conduit 526 disposed through the fistula and the head 524 disposed adjacent the proximal end of the fistula, or the hollow working member 536 may be further advanced to push the conduit 526 into the fistula. The hollow working member 536 may then be retracted and disengaged from the implant device 522 to leave the implant device 522 in the implanted position.

Figure 19:
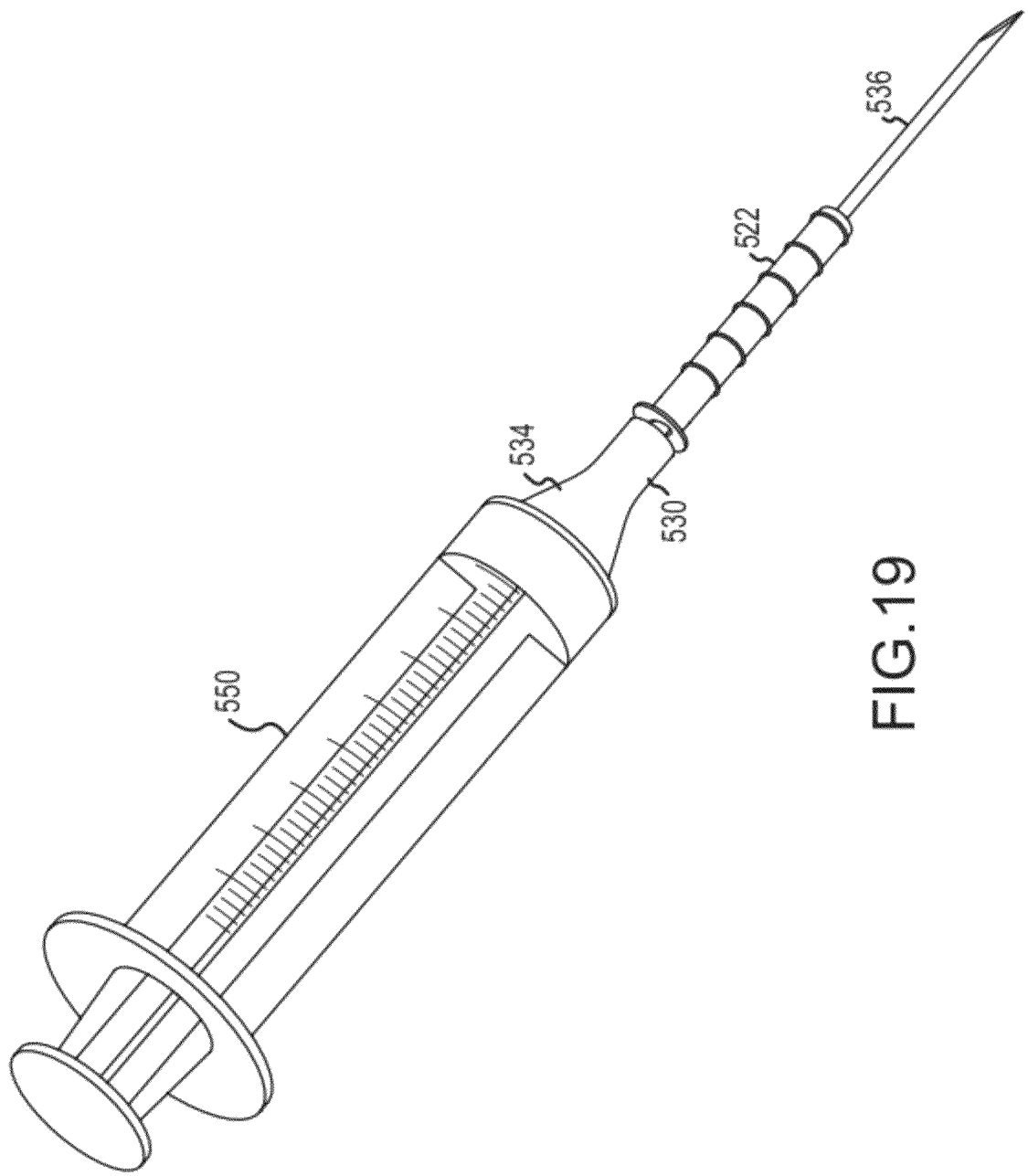
FIG. 19 is a perspective view showing a first carrier piece of the same embodiment of a tool shown in FIGS. 17 and 18, with the first carrier piece connected with a syringe.

Continuing with reference to FIGS. 17 and 18, the hollow working member 536 facilitates performance of an ancillary medical procedure involving aspirating fluid from or introducing fluid into the paranasal sinus. For example, before or after positioning the implant device 522 in the proper location for implantation, the second carrier piece 532 may be disengaged from the first carrier piece 534 to remove the solid working member 542 from the hollow interior of the hollow working member 536. The hollow working member 536 is then available for aspiration of fluid from or injection of fluid into the paranasal sinus. The hub 534 may be engaged with a corresponding connection structure of a syringe and the syringe may be operated to aspirate fluid from the paranasal sinus into the syringe or to inject fluid from the syringe into the paranasal sinus. Fluids that may be injected into the paranasal sinus include irrigation fluid or treatment compositions containing a drug, for example to inject a drug bolus for treatment of sinusitis. As used herein, "fluid" includes flowable compositions, including compositions that may have a solid material dispersed or suspended in a fluid medium. After the implant device has been properly positioned for implantation and after performing any desired ancillary medical procedure, the first carrier pierce may be retracted to disengage the hollow working member 536 from the internal passage of the implant device 522 and to leave the implant device 522 as an implant. FIG. 19 shows the first carrier piece 536 of the surgical tool 500 connected with a syringe 550.

Referring now to FIGS. 20-25, some additional examples of surgical procedures involving forming a fistula and implanting an implant device, and some example surgical tools for use therewith, will now be described.

Figure 20:
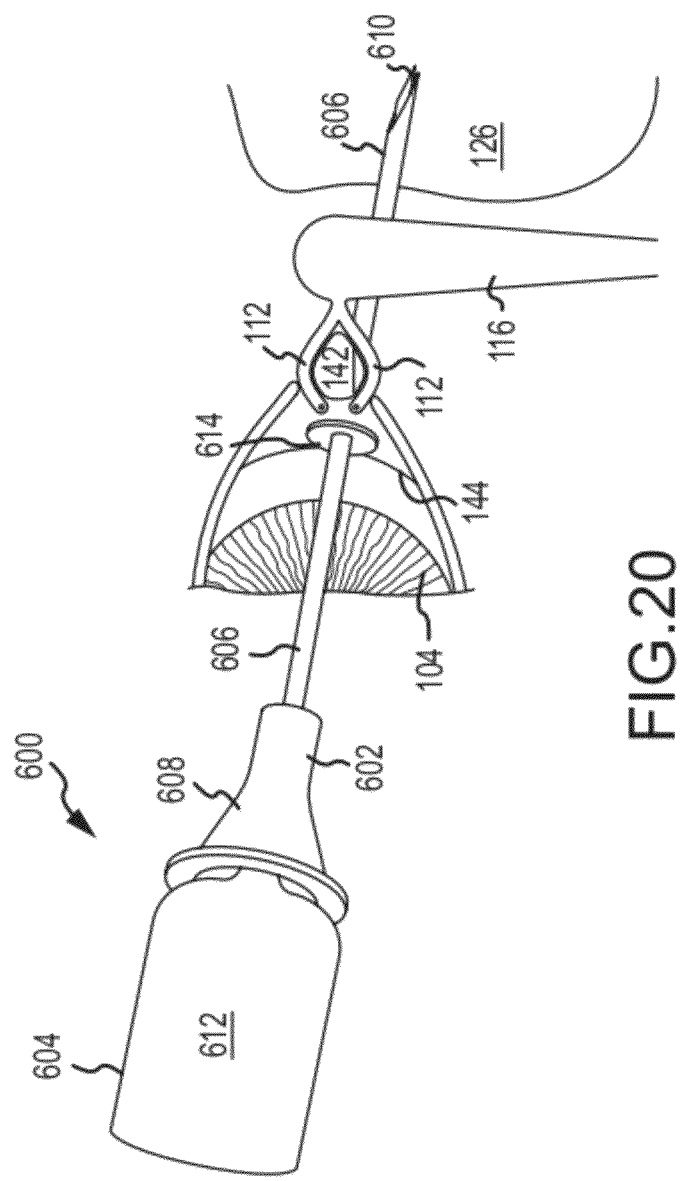
FIG. 20 is an illustration showing use of a surgical tool to form a fistula between the orbit and an ethmoid sinus during a surgical procedure.

In FIG. 20 a surgical tool in the form of an entry tool 600 is shown in the process of making a fistula through tissue between the lacrimal caruncle 142 and the plica semilunaris 144. Numbering of anatomical parts is the same as in FIGS. 1 and 3. The fistula is formed through tissue between the conjunctival sac in the orbit and the ethmoid sinus 126. The route for the fistula would be consistent with general fistula route 132 as shown in FIG. 3. The entry tool 600 includes a first piece 602 and a second piece 604. The first piece 602 includes a hollow working member 606 and a hub 608. The second piece 604 includes a solid working member (not shown) disposed through a hollow interior of the hollow working member 606. A distal tip portion of the hollow working member 606 of the first piece 602 and a distal tip portion of the solid working member of the second piece 604 form a distal tip 610 with a shape suitable for insertion through the tissue to form a fistula from the conjunctival sac to the ethmoid sinus 126. The second piece 604 includes a hand-manipulable handle 612. The hub 608 may be configured for connecting with a syringe or other fluid manipulation device, such as through a luer connection. The handle 612 may be retracted relative to the hub 608 to remove the solid working member from the interior of the hollow working member 606 and to disengage the second piece 604 from the first piece 602. As shown in FIG. 20, the distal tip 610 has been advanced from a location in the conjunctival sac between the caruncle 142 and the plica semilunaris 144 to form a fistula between the conjunctival sac and the ethmoid sinus 126. As shown, the fistula passes behind the caruncle 142, canaliculi 112 and nasolacrimal duct 116 to access the ethmoid sinus 126. The first piece 602 of the entry tool 600 includes a collar stop 614 to prevent the hollow working member 606 from being advanced through tissue beyond a certain distance. The first piece 602 and the second piece 604 may, for example, be substantially the same as the first carrier piece 530 and the second piece 532 of the tool assembly 520 of FIG. 17, but with the added collar stop 614 and not including an implant device mounted thereon.

Figure 21:
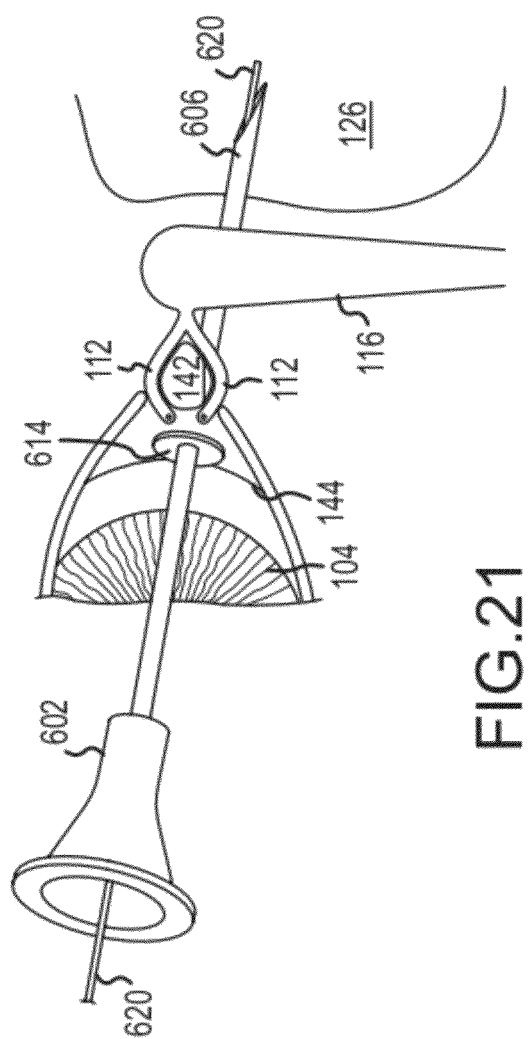
FIG. 21 is an illustration showing insertion of a guide wire following formation of the fistula during a surgical procedure.
Figure 22:
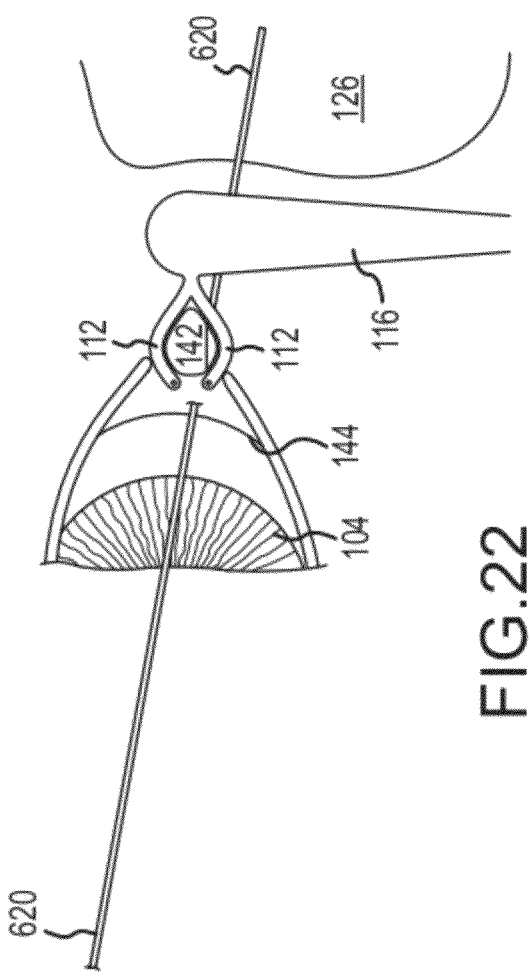
FIG. 22 is an illustration showing a guide wire in place as a guide to a fistula during a surgical procedure.

After the entry tool 600 has been used to initially form a fistula to the ethmoid sinus 126, then the second piece 604 may be disengaged from the first piece 602 and a guide wire inserted through the internal passage through the hollow working member 606. FIG. 21 shows the first piece 602 after disengagement of the second piece 604 and after insertion of a guide wire 620 through the first piece 602 and exiting from a distal end of the first piece 602 in the ethmoid sinus 126. After insertion of the guide wire 620, the first piece 602 may be retracted and removed from the fistula, leaving the guide wire 620 in place as a guide to and through the fistula. FIG. 22 shows the guide wire 620 disposed through the fistula after removal of the first piece 602. The guide wire 620 is now available for guiding additional tools to and through the fistula into the ethmoid sinus 126.

Figure 23:
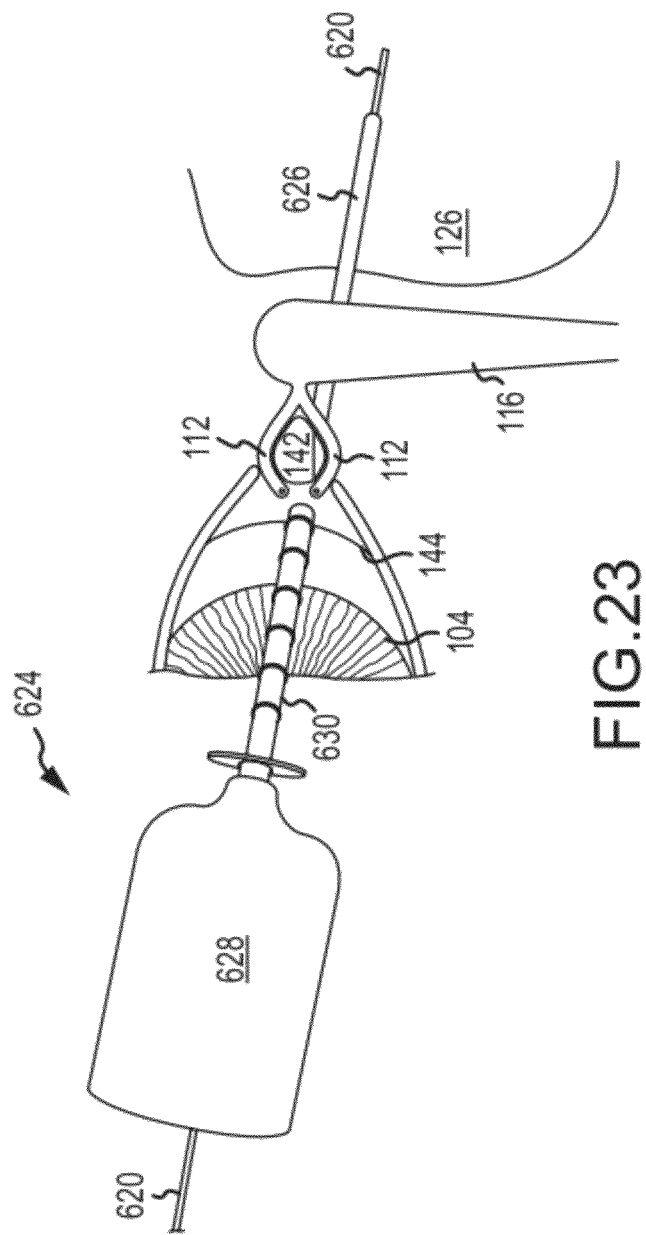
FIG. 23 is an illustration showing use of a surgical tool for implantation of an implant device during a surgical procedure.
Figure 24:
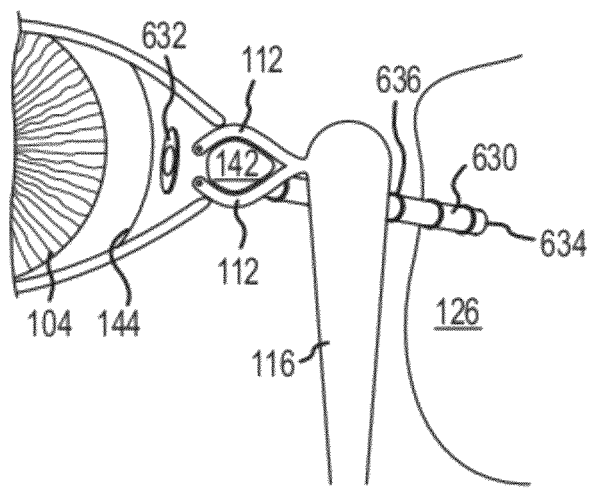
FIG. 24 is an illustration showing placement of an implant device following implantation during a surgical procedure.

With reference now to FIG. 23, the guide wire 620 has been used to guide a surgical tool, in the form of an implant tool 624. The implant tool 624 includes a hollow working member 626 and a hand-manipulable handle 628. The implant tool 624 includes an internal passage passing through the handle 628 and the hollow working member 626. As shown in FIG. 23, the guide wire 620 has been threaded through the internal passage of the implant tool 624 to guide the hollow working member 626 to and through the fistula and into the ethmoid sinus 126. The implant tool 624 also includes an implant device 630 mounted on the hollow working member 626. FIG. 23 shows the implant tool 624 advanced to a point where the distal end of the implant device 630 is in the vicinity of the proximal end of the fistula opening into the conjunctival sac. From this position, the implant device 630 may be advanced into the fistula with a head of the implant device 630 disposed adjacent the conjunctiva in the conjunctival sac and a distal end of the implant device 630 extending into the ethmoid sinus 626. The implant tool 624 may, for example, be a tool of the design such as that shown for the surgical tool 500 in FIG. 16, with a hollow needle for the working needle 518. The implant device 630 of the implant tool 624 may, for example, have features as described with respect to any of FIGS. 4-19. With the continued reference to FIG. 23, the hollow working member 626 of the tool 624 preferably includes a blunt tip. The handle 628 and the hollow working member 626 form a carrier for the implant device 630. The handle 628 may be retracted and the hollow working member 626 disengaged from the implant device 630 after the implant device has been appropriately positioned for implantation through the fistula. As an alternative to the configuration of the implant tool 624 as shown in FIG. 23, the implant tool 624 could be configured to include a hub for connection (e.g., through a luer connection) with a syringe of other fluid manipulation device. For example, the implant tool 624 could be configured with a hub in a manner similar to the configuration of the first piece 602 shown in FIG. 21 and with the implant device appropriately mounted for implantation. As another variation on the configuration of the implant tool 624, the working member 626 could be fitted with a collar stop (e.g., as shown in FIG. 21) or other mounting aid against which the implant device 630 could be disposed to provide some additional distance between a proximal end of the implant device 630 and the handle 628. FIG. 24 shows the implant device 630 as implanted and following disengagement of the hollow working member 626 of the implant tool 628. As implanted, a head 632 at the proximal end of the implant device 630 is located adjacent the conjunctiva in the conjunctival sac within the orbit between the caruncle 142 and the plica semilunaris 144 and the distal end 634 of the implant device 630 is located in the paranasal sinus 626. Some of anchor protrusions 636 are disposed within the fistula to engage tissue and help anchor the implant device 630.

The procedure as described with reference to FIGS. 20-24 permits the working member 606 of the entry tool 600 to have a larger diameter working member 626 to form a fistula of appropriate size for accommodating the implant device 630 which is then implanted in a separate step using the implant tool 624 with the implant device 630 carried on to the working member 626, which may advantageously have a smaller diameter then the working member 606 used to form the fistula. As an alternative, an intermediate step to dilate the fistula to a desired size for implantation may be performed between initially forming the fistula with the entry tool 600 and implanting the implant device 630 using the implant tool 624. FIG. 25 shows a surgical tool in the form of a dilator tool 640 having a hollow working member 642 and a hand-manipulable handle 644. The working member 642 is disposed through the fistula, guided by the guide wire 620 passing through an internal passage through the dilator tool 640. As shown in FIG. 25, the working member 642 has been advanced to the point where a stop collar 646 attached to the working member 642 has engaged conjunctival tissue in the conjunctival sac adjacent a proximal end of the fistula. For this alternative implementation, the hollow working member 642 of the dilator tool 640 would have a larger diameter than the hollow working member 606 of the entry tool 600 shown in FIGS. 20 and 21. The hollow working member 642 of the dilator tool 640, therefore widens the fistula further to a desired size to accommodate easier insertion of the implant device 630. Although the intermediate step of dilation as shown is not required, it permits the use of a smaller-diameter working member 606 during initial formation of the fistula. The use of a smaller diameter for the working member 606 to initially form the fistula permits better visibility and procedural control for a surgeon performing the procedure. The working member 642 may preferably include a blunt tip.

In a method for providing access to a paranasal sinus to a human to permit performance of medical treatments or procedures in the paranasal sinus over an extended time, a surgically formed, durably patent fistula may be created between the lacrimal apparatus of the human and the paranasal sinus. By surgically formed, it is mean that the fistula is an artificial passage through tissue that is intentionally formed by a surgical operation. For example, the fistula may be formed using a trocar, stylet, needle or cannula. The fistula may be formed by a surgical tool as described with reference to any of FIGS. 16-19. By "durably patent" it is meant that the fistula is resistant to closure by natural tissue repair mechanisms and remains open (patent) for an extended period of time to provide access into the paranasal sinus over the extended period of time. The extended period of time may be any period of time sufficient for performing through the fistula any desired medical treatments or procedures. The extended period of time may, for example, be at least 7 days, at least 14 days, at least 30 days, at least 180 days, or longer. The extended period may be permanent.

A fistula may be maintained as durably patent for an extended period of time by a variety of techniques. As one example for maintaining fistula patency, an implant device may be disposed through the fistula to prevent the fistula from closing, and the implant device may include an internal passage for providing access through the fistula into the paranasal sinus. When access to the paranasal sinus is no longer required, the implant device may be removed to permit tissue to repair and close the fistula. The implant device may, for example, have a configuration as described with respect to any of FIGS. 4-19 or may have a different configuration. As another example for maintaining fistula patency, the fistula may be formed initially with a relatively large diameter, and preferably with a clean cut. A large, cleanly cut hole will naturally tend to remain patent and not repair for at least a significant time. The relatively large diameter of the fistula may, for example be at least 2 millimeters or larger, as described above. When the fistula is formed with such a large diameter, the fistula will preferably be formed at a location in the nasolacrimal duct. As another example for maintaining fistula patency, after the fistula is formed the tissue adjacent the fistula may be mechanically treated to form a mechanical impediment to tissue repair that would close the fistula. The mechanical treatment could involve, for example over-sewing tissue adjacent the fistula or stapling tissue adjacent the fistula to mechanically retain the tissue in a manner to inhibit tissue repair that would close the fistula. As another example for maintaining fistula patency, tissue adjacent the fistula may be treated with a substance (e.g., a drug) effective to inhibit natural tissue repair and closure of the fistula, such as for example treatment with an antigranulation or anti-scarring agent (e.g., steroids, Mitomycin C).

A variety of medical treatments and procedures may be performed through a fistula formed between the lacrimal apparatus and a paranasal sinus, whether or not the fistula is durably patent. One or more medical devices may be inserted into the paranasal sinus through the fistula. For example a hollow working member (e.g., hollow needle, cannula) may be inserted through the fistula into the paranasal sinus to permit aspiration of fluid from or injection of a treatment formulation (e.g., drug formulation, irrigation fluid) into the paranasal sinus. As another example, a treatment formulation (e.g., drug formulation, irrigation fluid) may be transmitted through the fistula into the paranasal sinus by natural flow from the lacrimal system. A treatment formulation may be administered to the vicinity of the eye (e.g., as eye drops) to naturally flow from the lacrimal apparatus through the fistula and into the paranasal sinus. The fistula may, but need not necessarily be, a durably patent fistula. For example, a conduit of a medical device be inserted from the lacrimal apparatus through tissue and into the paranasal sinus, fluid may be aspirated through or injected from the conduit, and the conduit may then be removed to allow the fistula formed by insertion of the conduit to quickly repair. Such a conduit may, for example, be a hypodermic needle or cannula (e.g., connected to a syringe, drip system or other fluid injection/aspiration system). The fistula may be formed by insertion of a member including the needle or cannula and may naturally repair and close quickly following removal of the conduit. For example, the fistula may be formed by insertion of a hypodermic needle, a fluid may be injected or aspirated through the hypodermic needle and the hypodermic needle may then be removed to permit the fistula to repair. As another example, the fistula may be formed by a trocar/cannula assembly, the trocar may then be removed, a medical procedure performed through the cannula (e.g., fluid injection or aspiration), and the cannula may then be removed to permit the fistula to repair. As another example, the fistula may be formed by a cutting cannula, a medical procedure performed through the cannula (e.g., fluid injection or aspiration), and the cannula may then be removed to permit the fistula to repair.

A surgically created, durably patent fistula may be advantageously located for transmitting lacrimal fluid (tears) to a paranasal sinus. Lacrimal fluid from the lacrimal apparatus may be permitted to drain into the paranasal sinus. In one preferred implantation, the surgically-created, durably patent fistula is from either the orbit or the nasolacrimal duct to either the ethmoid sinus or the maxillary sinus, with a fistula route from the orbit being more preferred.

The foregoing discussion of the invention and different aspects thereof has been presented for purposes of illustration and description. The foregoing is not intended to limit the invention to only the form or forms specifically disclosed herein. Consequently, variations and modifications commensurate with the above teachings, and the skill or knowledge of the relevant art, are within the scope of the present invention.

The embodiments described hereinabove are further intended to explain best modes known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art. Although the description of the invention has included description of one or more possible implementations and certain variations and modifications, other variations and modifications are within the scope of the invention, e.g., as may be within the skill and knowledge of those in the art after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. Furthermore, any feature described or claimed with respect to any disclosed implementation may be combined in any combination with one or more of any other features of any other implementation or implementations, to the extent that the features are not necessarily technically incompatible, and all such combinations are within the scope of the present invention.

The terms "comprising", "containing", "including" and "having", and grammatical variations of those terms, are intended to be inclusive and nonlimiting in that the use of such terms indicates the presence of some condition or feature, but not to the exclusion of the presence also of any other condition or feature. The use of the terms "comprising", "containing", "including" and "having", and grammatical variations of those terms in referring to the presence of one or more components, subcomponents or materials, also include and is intended to disclose the more specific embodiments in which the term "comprising", "containing", "including" or "having" (or the variation of such term) as the case may be, is replaced by any of the narrower terms "consisting essentially of" or "consisting of" or "consisting of only" (or the appropriate grammatical variation of such narrower terms). For example, a statement that some thing "comprises" a stated element or elements is also intended to include and disclose the more specific narrower embodiments of the thing "consisting essentially of" the stated element or elements, and the thing "consisting of" the stated element or elements. Examples of various features have been provided for purposes of illustration, and the terms "example", "for example" and the like indicate illustrative examples that are not limiting and are not to be construed or interpreted as limiting a feature or features to any particular example. The term "at least" followed by a number (e.g., "at least one") means that number or more than that number. The term at "at least a portion" means all or a portion that is less than all. The term "at least a part" means all or a part that is less than all.

What is claimed is:

1. A method for providing access to a paranasal sinus of a human to permit performance of medical treatments or procedures in the paranasal sinus over an extended time, the method comprising creating a surgically formed, durably patent fistula between a lacrimal apparatus of the human and the paranasal sinus;

the creating a surgically formed, durably patent fistula comprises implanting an implant device with a conduit disposed through the fistula to maintain patency of the fistula;

the implant device comprises a proximal end at a first longitudinal end of the implant device, a distal end at a second longitudinal end of the implant device that is longitudinally opposite the first longitudinal end, the conduit between the proximal end and the distal end and an internal passage extending through the conduit;

the fistula is between the lacrimal apparatus in the orbit and the paranasal sinus, wherein the paranasal sinus is selected from the group consisting of an ethmoid sinus, a maxillary sinus and a frontal sinus;

the implanting comprises positioning the implant device in an implantation position with the conduit disposed through the fistula and with the internal passage opening at a first end into the lacrimal apparatus in the orbit and opening at a second end into the paranasal sinus to provide fluid communication through the internal passage between the lacrimal apparatus in the orbit and the paranasal sinus;

the conduit comprises an exterior with an anchoring surface feature including protrusion areas and recess areas; and in the implantation position at least a portion of the recess areas are disposed within the fistula and at least a portion of the protrusion areas are disposed in the fistula engaging tissue exposed within the fistula to anchor the implant device.

2. A method according to claim 1, wherein:

the conduit extends from adjacent the proximal end to adjacent the distal end;

the internal passage extends between the proximal end of the implant device and the distal end of the implant device and through the conduit, the internal passage having a first end open at the proximal end and a second end open at the distal end;

a length longitudinally along the implant device between the proximal end and the distal end is in a range of from 2 millimeters to 50 millimeters; and a width of the internal passage transverse to the length is in a range of from 0.25 millimeter to 5 millimeters.

3. A method according to claim 1, comprising performing at least one procedure through a hollow member disposed through the fistula, the procedure selected from the group consisting of introducing a drug formulation into the paranasal sinus from the hollow member, introducing an irrigation fluid into the paranasal sinus from the hollow member and aspiration of fluid from the paranasal sinus through the hollow member.

4. A method according to claim 1, comprising performing a procedure through the fistula directed to treatment for sinusitis.

5. A method according to claim 1, comprising aspirating fluid from the paranasal sinus through the fistula.

6. A method according to claim 1, comprising irrigating the paranasal sinus with an irrigation fluid introduced into the paranasal sinus through the fistula.

7. A method according to claim 1, comprising introducing a drug formulation into the paranasal sinus through the fistula.

8. A method for delivering a treatment formulation to a paranasal sinus of a human, the method comprising administering the treatment formulation for delivery to the paranasal sinus through a conduit of an implant device disposed through a fistula formed between a lacrimal apparatus of the human and the paranasal sinus, the conduit comprising an exterior with an anchoring surface feature including protrusion areas and recess areas and at least a portion of the recess areas are disposed within the fistula and at least a portion of the protrusion areas are disposed in the fistula engaging tissue exposed within the fistula to anchor the implant device.

9. A method according to claim 8, wherein the administering comprises introducing the treatment formulation into the paranasal sinus from a hollow member disposed through the fistula.

10. A method according to claim 8, wherein the administering comprises administering the treatment formulation to the vicinity of an eye to flow through the conduit and into the paranasal sinus.

11. A method for delivering a treatment formulation to a paranasal sinus of a human, the method comprising administering the treatment formulation for delivery to the paranasal sinus through a fistula formed between a lacrimal apparatus of the human and the paranasal sinus, the administering comprising administering the treatment formulation to the vicinity of an eye to flow through the fistula and into the paranasal sinus, wherein the treatment formulation is in the form of an ophthalmic composition administered as eye drops.

12. A method according to claim 11, wherein the administering results in delivery of the treatment formulation to the paranasal sinus through a conduit of an implant device disposed through the fistula.

13. A method according to claim 11, wherein the fistula is a surgically created, durably patent fistula.

14. A method according to claim 8, wherein the treatment formulation comprises a drug formulation for treatment of sinusitis.

15. A method according to claim 8, wherein the treatment formulation comprises at least one drug selected from the group consisting of anti-inflammatories, antimicrobials, analgesics, mucolytics, antivirals, decongestants and antifungals.

16. A method according to claim 8, wherein the treatment formulation comprises at least one drug selected from the group consisting of steroids and antihistamines.

17. A method according to claim 8, wherein the treatment formulation comprises an antibiotic.

18. A method according to claim 8, wherein the treatment formulation comprises an irrigation fluid to irrigate the paranasal sinus.

19. A method according to claim 8, wherein the fistula is between the lacrimal apparatus in the orbit and a paranasal sinus selected from the group consisting of an ethmoid sinus, a maxillary sinus and a frontal sinus.

20. A method according to claim 8, wherein the fistula is between the lacrimal apparatus in the orbit and an ethmoid sinus.

21. A method according to claim 8, wherein the fistula is between the nasolacrimal duct and either an ethmoid sinus or a maxillary sinus.

22. A method for treating a paranasal sinus of a human, the method comprising transmitting lacrimal fluid from a lacrimal apparatus through a surgically formed, durably patent fistula between a lacrimal apparatus of the human and the paranasal sinus;
wherein patency of the fistula is maintained by an implant device disposed through the fistula, the implant device comprising an internal passage providing fluid communication between the lacrimal apparatus and the paranasal sinus for conducting lacrimal fluid from the lacrimal apparatus to the paranasal sinus; and
wherein the conduit comprises an exterior with an anchoring surface feature including protrusion areas and recess areas and at least a portion of the recess areas are disposed within the fistula and at least a portion of the protrusion areas are disposed in the fistula engaging tissue exposed within the fistula to anchor the implant device.

23. A method for performing a medical procedure in a paranasal sinus, the method comprising aspirating fluid from or introducing fluid into the paranasal sinus through a conduit of an implant device while the conduit is disposed through a fistula between the lacrimal apparatus and the paranasal sinus, the conduit comprising an exterior with an anchoring surface feature including protrusion areas and recess areas and at least a portion of the recess areas are disposed within the fistula and at least a portion of the protrusion areas are disposed in the fistula engaging tissue exposed within the fistula to anchor the implant device.

24. A method according to claim 23, wherein the conduit comprises a hollow member disposed through the fistula with a tip of the hollow member disposed within the paranasal sinus.

25. A method according to claim 23, comprising introducing the fluid into the paranasal sinus, and wherein the fluid comprises a drug formulation for treatment of sinusitis.

26. A method for providing access to a paranasal sinus of a human to permit performance of medical treatments or procedures in the paranasal sinus over an extended time, the method comprising creating a surgically formed, durably patent fistula between a lacrimal apparatus of the human and the paranasal sinus;
the creating a surgically formed, durably patent fistula comprises implanting an implant device with a conduit disposed through the fistula to maintain patency of the fistula;
the implant device comprises a proximal end at a first longitudinal end of the implant device, a distal end at a second longitudinal end of the implant device that is longitudinally opposite the first longitudinal end, the conduit between the proximal end and the distal end and an internal passage extending through the conduit;
the fistula is between the lacrimal apparatus in the orbit and the paranasal sinus, wherein the paranasal sinus is selected from the group consisting of an ethmoid sinus, a maxillary sinus and a frontal sinus;
the implanting comprises positioning the implant device in an implantation position with the conduit disposed through the fistula and with the internal passage opening at a first end into the orbit and opening at a second end into the paranasal sinus to provide fluid communication through the internal passage between the lacrimal apparatus in the orbit and the paranasal sinus the implant device comprises a head adjacent the conduit at the proximal end of the implant device, the head having a length dimension and a width dimension transverse to the length dimension with a ratio of the length dimension to the width dimension being at least 1.5;
the head comprises a flanged tissue engagement surface on a side of the head disposed toward the conduit; and
in the implantation position, the tissue engagement surface is engaged with tissue in the orbit adjacent to the fistula.

27. A method according to claim 26, wherein in the implantation position the length dimension of the head extends in a direction from a bottom of the orbit toward a top of the orbit.

28. A method according to claim 1, wherein in the implantation position at least a portion of the protrusion areas and at least a portion of the recess areas are disposed in the paranasal sinus.

29. A method according to claim 28, wherein the protrusion areas are on a longitudinal portion of the conduit extending at least 5 millimeters along a length of the implant device.

30. A method according to claim 28, wherein the implant device comprises a head adjacent the conduit at the proximal end of the implant device, the head having a length dimension and a width dimension transverse to the length dimension with a ratio of the length dimension to the width dimension being at least 1.5;
the head comprises a flanged tissue engagement surface on a side of the head disposed toward the conduit; and
in the implantation position, the tissue engagement surface is engaged with tissue in the orbit adjacent to the fistula.

31. A method according to claim 30, wherein the protrusion areas are on a longitudinal portion of the conduit having a proximal end that is disposed at least 3 millimeters from the head.

32. A method according to claim 28, wherein:
the protrusion areas comprise at least 3 spaced circumferential ridges, with each said circumferential ridge extending around an entire circumference of the conduit;
the circumferential ridges have a center-to-center spacing in a range of from 1 millimeter to 2 millimeters; and
in the implantation position at least one of the circumferential ridges is disposed in the paranasal sinus.

33. A method according to claim 28, wherein:
the implant device is constructed of medical grade silicone having a durometer (Shore A) in a range of from 50 to 80.

34. A method according to claim 1, wherein the implanting comprises:
pushing a carrier tool on which the implant device is mounted to push the conduit through the fistula until the distal end exits from a distal end of the fistula into the paranasal sinus and the implant device is in the implantation position; and
after the implant device is in the implantation position, disengaging the carrier tool from the implant device leaving the implant device in the implantation position.

35. A method according to claim 1, comprising after the implanting, administering a drug formulation to the paranasal sinus through the internal passage of the implant device.

36. A method according to claim 8, wherein:
the fistula is between the lacrimal apparatus in the orbit and the paranasal sinus, wherein the paranasal sinus is selected from the group consisting of an ethmoid sinus, a maxillary sinus and a frontal sinus; and
the implant device comprises an internal passage extending through the conduit, the internal passage opening at a first end into the lacrimal apparatus in the orbit and opening at a second end into the paranasal sinus to provide fluid communication through the internal passage between the lacrimal apparatus in the orbit and the paranasal sinus.

37. A method according to claim 28, wherein the conduit has an exterior width defined by an extent of the protrusion areas transverse to the length that is within a range of from 1.5 millimeters to 3 millimeters.

38. A method according to claim 37, wherein the protrusion areas have a height relative to the recess areas in a range of from 0.2 millimeter to 0.75 millimeter.

39. A method according to claim 38, wherein the protrusion areas are on a longitudinal portion of the conduit extending at least 3 millimeters along a length of the implant device and the protrusion areas cover no more than 35 percent of the area along the longitudinal portion of the conduit.

40. A method according to claim 39, wherein the protrusion areas comprise multiple protrusion occurrences spaced on the exterior of the conduit; and
the protrusion occurrences have a center-to-center spacing in a range of from 1 millimeter to 2 millimeters.

41. A method according to claim 28, wherein the conduit has a length in a range of from 8 millimeters to 30 millimeters.

42. A method according to claim 30, wherein the length dimension of the head is in a range of from 2 millimeters to 8 millimeters.

43. A method according to claim 1, wherein:
the conduit has a length in a range of from 8 millimeters to 30 millimeters;
the protrusion areas are on a longitudinal portion of the conduit extending at least 3 millimeters along a length of the implant device;
the conduit has an exterior width defined by an extent of the protrusion areas transverse to the length that is within a range of from 1.5 millimeters to 3 millimeters;
the protrusion areas have a height relative to the recess areas in a range of from 0.2 millimeter to 0.75 millimeter; and
the protrusion areas are constructed of medical grade silicone having a durometer (Shore A) in a range of from 50 to 80.

44. A method according to claim 35, wherein the drug formulation comprises at least one drug selected from the group consisting of anti-inflammatories, antimicrobials, analgesics, mucolytics, antivirals, decongestants and antifungals.

45. A method according to claim 35, wherein the drug formulation comprises a steroid.

46. A method according to claim 35, wherein the drug formulation comprises an antihistamine.

47. A method according to claim 35, wherein the drug formulation comprises an antibiotic.

48. A method according to claim 8, wherein:
the conduit has a length in a range of from 8 millimeters to 30 millimeters;
the protrusion areas are on a longitudinal portion of the conduit extending at least 5 millimeters along a length of the implant device;
the conduit has an exterior width defined by an extent of the protrusion areas transverse to the length that is within a range of from 1.5 millimeters to 3 millimeters; and
the protrusion areas have a height relative to the recess areas in a range of from 0.2 millimeter to 0.75 millimeter.

49. A method according to claim 48, wherein the implant device comprises a head adjacent the conduit at the proximal end of the implant device, the head comprising a flanged tissue engagement surface on a side of the head disposed toward the conduit; and
in the implantation position, the tissue engagement surface is engaged with tissue in the orbit adjacent to the fistula.

50. A method according to claim 49, wherein:
the head has a length dimension and a width dimension transverse to the length dimension, with a ratio of the length dimension to the width dimension being at least 1.5; and
length dimension of the head is in a range of from 2 millimeters to 8 millimeters.

51. A method according to claim 49, wherein the protrusion areas are on a longitudinal portion of the conduit having a proximal end that is disposed at least 3 millimeters from the head.

52. A method according to claim 8, wherein the protrusion areas comprise at least 3 spaced circumferential ridges, with each said circumferential ridge extending around an entire circumference of the conduit.

53. A method according to claim 52, wherein the circumferential ridges have a center-to-center spacing in a range of from 0.5 millimeter to 2.5 millimeters.

54. A method according to claim 53, wherein the circumferential ridges have a height relative to the recess areas in a range of from 0.2 millimeter to 1 millimeter.

55. A method according to claim 52, wherein the circumferential ridges are constructed of medical grade silicone having a durometer (Shore A) in a range of from 50 to 80.

56. A method according to claim 8, wherein the protrusion areas are on a longitudinal portion of the conduit extending at least 3 millimeters along a length of the implant device and the protrusion areas cover no more than 35 percent of the area along the longitudinal portion of the conduit.

57. A method according to claim 8, wherein the treatment formulation comprises a steroid.

58. A method according to claim 8, wherein the treatment formulation comprises an antihistamine.

59. A method according to claim 11, wherein the fistula is between the lacrimal apparatus in the orbit and a paranasal sinus selected from the group consisting of an ethmoid sinus, a maxillary sinus and a frontal sinus.

60. A method according to claim 11, wherein the fistula is between the nasolacrimal duct and either an ethmoid sinus or a maxillary sinus.

61. A method according to claim 13, wherein tissue adjacent the fistula has been treated with a substance effective to inhibit natural repair of the fistula.

62. A method according to claim 61, wherein the substance comprises at least one member selected from the group consisting of antigranulation agents and anti-scarring agents.

63. A method according to claim 13, wherein tissue adjacent the fistula is over-sewn to maintain patency of the fistula.

64. A method according to claim 13, wherein tissue adjacent the fistula is stapled to maintain patency of the fistula.

65. A method according to claim 11, wherein the treatment formulation comprises at least one drug selected from the group consisting of anti-inflammatories, antimicrobials, analgesics, mucolytics, antivirals, decongestants and antifungals.

66. A method according to claim 11, wherein the treatment formulation comprises a steroid.

67. A method according to claim 11, wherein the treatment formulation comprises an antihistamine.

68. A method according to claim 11, wherein the treatment formulation comprises an antibiotic.

69. A method according to claim 26, wherein the wherein length dimension of the head is in a range of from 2 millimeters to 8 millimeters.

70. A method according to claim 69, wherein the width dimension of the head is in a range of from 1 millimeter to 4 millimeters.

71. A method according to claim 70, wherein the conduit has a length in a range of from 8 to 30 millimeters.

72. A method according to claim 70, wherein the head has a depth in a range of from 0.25 to 1 millimeter.

73. A method according to claim 70, wherein the implant device is constructed of medical grade silicone having a durometer (Shore A) in a range of from 50 to 80.

74. A method according to claim 26, wherein the fistula is between the lacrimal apparatus in the orbit and an ethmoid sinus.

* * * * *